(12) United States Patent
Oda et al.

(10) Patent No.: US 8,598,349 B2
(45) Date of Patent: Dec. 3, 2013

(54) METHOD FOR MANUFACTURING CONJUGATED AROMATIC COMPOUND

(75) Inventors: Seiji Oda, Ibaraki (JP); Takashi Kamikawa, Nara (JP); Akio Tanaka, Kobe (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/144,010

(22) PCT Filed: Jan. 18, 2010

(86) PCT No.: PCT/JP2010/050859
§ 371 (c)(1),
(2), (4) Date: Jul. 11, 2011

(87) PCT Pub. No.: WO2010/084976
PCT Pub. Date: Jul. 29, 2010

(65) Prior Publication Data
US 2011/0275859 A1    Nov. 10, 2011

(30) Foreign Application Priority Data

Jan. 23, 2009 (JP) ................................ 2009-012865

(51) Int. Cl.
*C07D 401/04* (2006.01)

(52) U.S. Cl.
USPC .................. 546/1; 546/66; 546/112; 568/309

(58) Field of Classification Search
USPC ............. 568/34, 309; 544/294; 528/167, 397; 558/411, 414; 546/167, 1, 66, 112
See application file for complete search history.

(56) References Cited

U.S. PATENT DOCUMENTS

| | | | |
|---|---|---|---|
| 4,990,647 A * | 2/1991 | Himmler et al. | 558/414 |
| 6,194,599 B1 * | 2/2001 | Miller et al. | 558/411 |
| 8,088,883 B2 * | 1/2012 | Asaumi et al. | 528/397 |
| 2006/0058524 A1 | 3/2006 | Falcou et al. | |
| 2010/0292481 A1 * | 11/2010 | Oda et al. | 546/167 |

FOREIGN PATENT DOCUMENTS

| | | |
|---|---|---|
| JP | 2745727 B2 | 4/1998 |
| JP | 2008-169263 A | 7/2008 |
| JP | 2008-201810 A | 9/2008 |
| JP | 2009-001629 A | 1/2009 |
| WO | WO 2007/102235 A1 | 9/2007 |
| WO | WO 2008/156196 A1 | 12/2008 |

OTHER PUBLICATIONS

International Preliminary Report of Patentability in PCT/JP2010/050859 dated Aug. 18, 2011.
Masahiko Iyoda et al., "Homocoupling of Aryl Halides Using Nickel (II) Complex and Zinc in the Presence of Et$_4$NI. An Efficient Method for the Synthesis of Biaryls and Bipyridines,"Bull. Chem. Soc. of Japan, vol. 63, No. 1, 1990, pp. 80-87.
International Search Report mailing date of Mar. 30, 2010 for International Application No. PCT/JP2010/050859.

* cited by examiner

*Primary Examiner* — Sudhakar Katakam
*Assistant Examiner* — Pancham Bakshi
(74) *Attorney, Agent, or Firm* — Foley & Lardner LLP

(57) ABSTRACT

A method for manufacturing a conjugated aromatic compound comprising reacting an aromatic compound (A) substituted with a halogen as a leaving group with an aromatic compound (A) or an aromatic compound (B) substituted with a halogen as a leaving group and is structurally different from the aromatic compound (A), in the presence of (i) a nickel compound, (ii) a metal reducing agent, (iii) at least one ligand (L1) selected from the group consisting of a 2,2'-bipyridine compound having at least one electron-withdrawing group, and a 1,10-phenanthroline compound having at least one electron-withdrawing group, and (iv) at least one ligand (L2) selected from the group consisting of a 2,2'-bipyridine compound having at least one electron-releasing group, and a 1,10-phenanthroline compound having at least one electron-releasing group.

18 Claims, No Drawings

METHOD FOR MANUFACTURING CONJUGATED AROMATIC COMPOUND

TECHNICAL FIELD

The present invention relates to a method for manufacturing a conjugated aromatic compound.

BACKGROUND ART

Conjugated aromatic compounds are important compounds in various fields such as agrochemicals, pharmaceuticals and electronic materials. As the method for manufacturing it, US 2006/0058524 A1 discloses a method comprising conducting a coupling reaction of an aromatic halide compound in the presence of a zero-valent nickel complex catalyst having 2,2'-bipyridine and 1,5-octadiene as ligands and a reducing agent.

DISCLOSURE OF THE INVENTION

The present invention provides:
<1> A method for manufacturing a conjugated aromatic compound comprising reacting an aromatic compound (A) wherein one or two leaving groups selected from the group consisting of an iodine atom, a bromine atom and a chlorine atom are bonded to an aromatic ring and the aromatic compound (A) does not have
(c1) a group represented by the following formula (10):

wherein $A^1$ represents an amino group substituted with one or two C1-C20 hydrocarbon groups, or a C1-C20 alkoxy group, and the above-mentioned hydrocarbon group and the above-mentioned alkoxy group may be substituted with at least one group selected from the group consisting of a fluorine atom, a C1-C20 alkoxy group, a C6-C20 aryl group, a C6-C20 aryloxy group, a C2-C20 acyl group and a C6-C20 arylsulfonyl group;
(g1) a C1-C20 alkyl group which may be substituted with at least one substituent selected from the group consisting of a fluorine atom, a cyano group, a C1-C20 alkoxy group, a 06-020 aryl group and a C6-C20 aryloxy group; and
(h1) a C2-C20 acyl group which may be substituted with at least one substituent selected from the group consisting of a fluorine atom, a cyano group, a C1-C20 alkoxy group, a C6-C20 aryl group and a C6-C20 aryloxy group,
at the neighboring carbon atom to the carbon atom to which the leaving group is bonded,
with an aromatic compound (A) having the same structure as that of the above-mentioned aromatic compound (A) or an aromatic compound (B) wherein the aromatic compound (B) is structurally different from the above-mentioned aromatic compound (A), one or two leaving groups selected from the group consisting of an iodine atom, a bromine atom and a chlorine atom are bonded to an aromatic ring and the aromatic compound (B) does not have the above-mentioned (c1), (g1) and (h1) at the neighboring carbon atom to the carbon atom to which the leaving group is bonded, in the presence of
(i) a nickel compound,
(ii) a metal reducing agent,
(iii) at least one ligand (L1) selected from the group consisting of a 2,2'-bipyridine compound having at least one electron-withdrawing group and having no substituent at 3-, 6-, 3'- and 6'-positions, and a 1,10-phenanthroline compound having at least one electron-withdrawing group and having no substituent at 2- and 9-positions, and
(iv) at least one ligand (L2) selected from the group consisting of a 2,2'-bipyridine compound having at least one electron-releasing group and having no substituent at 3-, 6-, 3'- and 6'-positions, and a 1,10-phenanthroline compound having at least one electron-releasing group and having no substituent at 2- and 9-positions;
<2> The method according to <1>, wherein the ligand (L1) is at least one ligand selected from the group consisting of a 2,2'-bipyridine compound having at least two electron-withdrawing groups and having no substituent at 3-, 6-, 3'- and 6'-positions, and a 1,10-phenanthroline compound having at least two electron-withdrawing groups and having no substituent at 2- and 9-positions;
<3> The method according to <1>, wherein the ligand (L1) is a 2,2'-bipyridine compound having at least two electron-withdrawing groups and having no substituent at 3-, 6-, 3'- and 6'-positions;
<4> The method according to any one of <1> to <3>, wherein the ligand (L2) is at least one ligand selected from the group consisting of a 2,2'-bipyridine compound having at least two electron-releasing groups and having no substituent at 3-, 6-, 3'- and 6'-positions, and a 1,10-phenanthroline compound having at least two electron-releasing groups and having no substituent at 2- and 9-positions;
<5> The method according to any one of <1> to <3>, wherein the ligand (L2) is a 2,2'-bipyridine compound having at least two electron-releasing groups and having no substituent at 3-, 6-, 3'- and 6'-positions;
<6> The method according to <2> or <3>, wherein the 2,2'-bipyridine compound having at least two electron-withdrawing groups and having no substituent at 3-, 6-, 3'- and 6'-positions is a bipyridine compound represented by the formula (1)

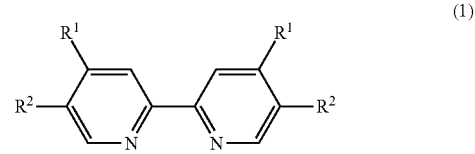

wherein $R^4$ and $R^2$ independently each represent a hydrogen atom or an electron-withdrawing group, with the proviso that $R^1$ and $R^2$ are not hydrogen atoms simultaneously;
<7> The method according to <2>, wherein the 1,10-phenanthroline compound having at least two electron-withdrawing groups and having no substituent at 2- and 9-position is a phenanthroline compound represented by the formula (2)

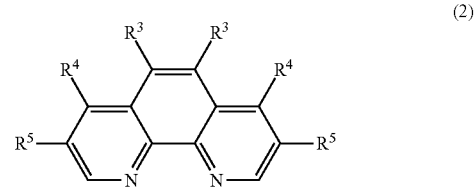

wherein R³, R⁴ and R⁵ independently each represent a hydrogen atom or an electron-withdrawing group, with the proviso that R³, R⁴ and R⁵ are not hydrogen atoms simultaneously;

<8> The method according to <4> or <5>, wherein the 2,2'-bipyridine compound having at least two electron-releasing groups and having no substituent at 3-, 6-, 3'- and 6'-positions is a bipyridine compound represented by the formula (3)

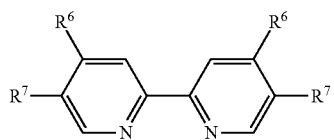

(3)

wherein R⁶ and R⁷ independently each represent a hydrogen atom or an electron-releasing group, with the proviso that R⁶ and R⁷ are not hydrogen atoms simultaneously;

<9> The method according to <4>, wherein the 1,10-phenanthroline compound having at least two electron-releasing groups and having no substituent at 2- and 9-positions is a phenanthroline compound represented by the formula (4)

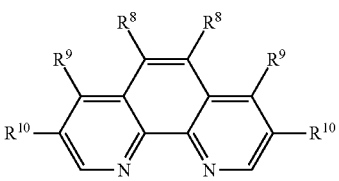

(4)

wherein R⁸, R⁹ and R¹⁰ independently each represent a hydrogen atom or an electron-releasing group, with the proviso that R⁸, R⁹ and R¹⁰ are not hydrogen atoms simultaneously;

<10> The method according to any one of <1> to <9>, wherein the electron-withdrawing group is a fluorine atom, a C1-C20 fluorinated alkyl group, a C2-C20 alkoxycarbonyl group, a C2-C20 acyl group, a cyano group or a nitro group;

<11> The method according to any one of <1> to <10>, wherein the electron-releasing group is a C1-C20 alkyl group, a C1-C20 alkoxy group, a C6-C20 aryl group or a C1-C20 dialkylamino group;

<12> The method according to any one of <1> to <11>, wherein the aromatic rings of the aromatic compound (A) and the aromatic compound (B) are independently a benzene ring, a biphenyl ring, a naphthalene ring, a fluorene ring, an anthracene ring, a phenanthrene ring, a thiophene ring, a pyrrole ring or a pyridine ring;

<13> The method according to any one of <1> to <12>, wherein an aromatic compound (A) is reacted with an aromatic compound (A) having the same structure as that of the aromatic compound (A);

<14> The method according to any one of <1> to <12>, wherein the aromatic compound (A) is reacted with an aromatic compound (B) being structurally different from the aromatic compound (A);

<15> The method according to any one of <1> to <14>, wherein the aromatic compound (A) is an aromatic compound represented by the formula (5)

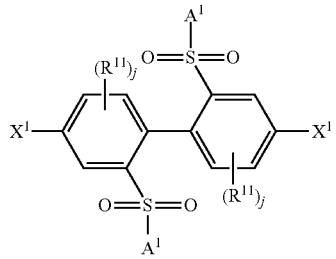

(5)

wherein $A^1$ represents an amino group substituted with one or two C1-C20 hydrocarbon groups, or a C1-C20 alkoxy group, and the above-mentioned hydrocarbon group and the above-mentioned alkoxy group may be substituted with at least one group selected from the group consisting of a fluorine atom, a C1-C20 alkoxy group, a C6-C20 aryl group, a C6-C20 aryloxy group, a C2-C20 acyl group and a C6-C20 arylsulfonyl group, $R^{11}$ is independently in each occurrence a fluorine atom, a C1-C20 alkyl group, a C1-C20 alkoxy group, a C6-C20 aryl group, a C6-C20 aryloxy group, a C2-C20 acyl group or a cyano group, and the above-mentioned C1-C20 alkyl group, the above-mentioned C1-C20 alkoxy group, the above-mentioned C6-C20 aryl group, the above-mentioned C6-C20 aryloxy group and the above-mentioned C2-C20 acyl group may be substituted with at least one substituent selected from the group consisting of a fluorine atom, a cyano group, a C1-C20 alkoxy group, a C6-C20 aryl group and a C6-C20 aryloxy group, and $R^{11}$s being bonded to the neighboring two carbon atoms may be bonded to form a ring, with the proviso that when $R^{11}$ is a C1-C20 alkyl group or a C2-C20 acyl group, $R^{11}$ is bonded to a carbon atom other than the neighboring carbon atoms to the carbon atom to which $X^1$ is bonded, $X^1$ represents a chlorine atom, a bromine atom or an iodine atom, and j represents an integer of 0 to 3;

<16> The method according to any one of <1> to <15>, wherein as the aromatic compound, an aromatic compound represented by the formula (6)

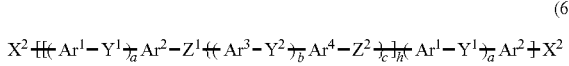

(6)

wherein a, b and c are the same or different and represent 0 or 1, and h represents an integer of 5 or more, $Ar^1$, $Ar^2$, $Ar^3$ and $Ar^4$ independently each represent a divalent aromatic group, and the divalent aromatic group may be substituted with at least one substituent selected from the group consisting of the following (a2) to (e2):

(a2) a C1-C20 alkyl group which may be substituted with at least one substituent selected from the group consisting of a fluorine atom, a cyano group, a C1-C20 alkoxy group, a C6-C20 aryl group and a C6-C20 aryloxy group;

(b2) a C1-C20 alkoxy group which may be substituted with at least one substituent selected from the group consisting of a fluorine atom, a cyano group, a C1-C20 alkoxy group, a C6-C20 aryl group and a C6-C20 aryloxy group;

(c2) a C6-C20 aryl group which may be substituted with at least one substituent selected from the group consisting of a fluorine atom, a cyano group, a C1-C20 alkoxy group and a C6-C10 aryloxy group;

(d2) a C6-C20 aryloxy group which may be substituted with at least one substituent selected from the group consisting of a fluorine atom, a cyano group, a C1-C20 alkoxy group and a C6-C20 aryloxy group; and (e2) a C2-C20 acyl group which may be substituted with at least one substituent selected from the group consisting of a fluorine atom, a cyano group, a C1-C20 alkoxy group, a C6-C20 aryl group and a C6-C20 aryloxy group, with the proviso that (a2) and (e2) are not bonded to the neighboring carbon atoms to the carbon atoms of $Ar^1$ and $Ar^2$ to which $X^2$ is bonded, $Y^1$ and $Y^2$ independently each represent a single bond, —CO—, —SO$_2$—, —C(CH$_3$)$_2$—, —C(CF$_3$)$_2$— or a fluorene-9,9-diyl group, $Z^1$ and $Z^2$ independently each represent —O— or —S—, and $X^2$ represents a chlorine atom, a bromine atom or an iodine atom, is used;

<17> The method according to any one of <1> to <16>, wherein the nickel compound is a nickel halide;

<18> The method according to any one of <1> to <16>, wherein the nickel compound is bis(cyclooctadiene) nickel (O);

<19> The method according to any one of <1> to <18>, wherein the metal reducing agent is zinc.

BEST MODE FOR CARRYING OUT THE PRESENT INVENTION

The aromatic compound (A) and the aromatic compound (B) compounds are compounds wherein they have at least one aromatic ring and one or two leaving groups selected from the group consisting of an iodine atom, a bromine atom and a chlorine atom are bonded to an aromatic ring.

The aromatic compound (B) is structurally different from the aromatic compound (A). Hereinafter, the aromatic compounds (A) and (B) are sometimes collectively described as the aromatic compound.

Examples of the aromatic ring include an aromatic hydrocarbon ring such as a benzene ring, a biphenyl ring, a naphthalene ring, a fluorene ring, an anthracene ring and a phenanthrene ring, and a heteroaromatic ring such as a thiophene ring, a pyrrole ring and a pyridine ring.

The aromatic compound (A) and the aromatic compound (B) are compounds wherein (c1) a group represented by the following formula (10):

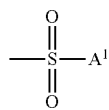

(10)

wherein $A^1$ represents an amino group substituted with one or two C1-C20 hydrocarbon groups, or a C1-C20 alkoxy group, and the above-mentioned hydrocarbon group and the above-mentioned alkoxy group may be substituted with at least one group selected from the group consisting of a fluorine atom, a C1-C20 alkoxy group, a C6-C20 aryl group, a C6-C20 aryloxy group, a C2-C20 acyl group and a C6-C20 arylsulfonyl group;

(g1) a C1-C20 alkyl group which may be substituted with at least one substituent selected from the group consisting of a fluorine atom, a cyano group, a C1-C20 alkoxy group, a C6-C20 aryl group and a C6-C20 aryloxy group; and (h1) a C2-C20 acyl group which may be substituted with at least one substituent selected from the group consisting of a fluorine atom, a cyano group, a C1-C20 alkoxy group, a C6-C20 aryl group and a C6-C20 aryloxy group, are not bonded to the neighboring carbon atom to the carbon atom to which the above-mentioned leaving group is bonded.

Examples of the C1-C20 hydrocarbon group in the formula (10) of (c1) include a C1-C20 linear, branched chain or cyclic alkyl group such as a methyl group, an ethyl group, a propyl group, an isopropyl group, a butyl group, an isobutyl group, a sec-butyl group, a tert-butyl group, a pentyl group, a 2,2-dimethylpropyl group, a hexyl group, a cyclohexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group and an icosyl group; a C6-C20 aryl group such as a phenyl group; a C4-C20 alkadienyl group such as a 1,3-butadiene-1,4-diyl group; a C1-C20 alkanediyl group such as a butane-1,4-diyl group and a pentane-1,5-diyl group; and a C6-C20 arylene group such as a biphenyl-2,2'-diyl group and an o-xylylene group. Examples of the amino group substituted with one or two C1-C20 hydrocarbon groups include a methylamino group, a dimethylamino group, an ethylamino group, a diethylamino group, a propylamino group, a dipropylamino group, an isopropylamino group, a diisopropylamino group, a butylamino group, a dibutylamino group, a sec-butylamino group, a di-sec-butylamino group, a tert-butylamino group, a di-tert-butylamino group, a pentylamino group, a 2,2-dimethylpropylamino group, a hexylamino group, a cyclohexylamino group, a heptylamino group, an octylamino group, a nonylamino group, a decylamino group, an undecylamino group, a dodecylamino group, a tridecylamino group, a tetradecylamino group, a pentadecylamino group, a hexadecylamino group, a heptadecylamino group, an octadecylamino group, a nonadecylamino group, an icosylamino group, a pyrrolyl group, a pyrrolidinyl group, a piperidinyl group, a carbazolyl group, a dihydroindolyl group and a dihydroisoindolyl group.

Examples of the C1-C20 alkoxy group in the formula (10) of (c1) include a C1-C20 linear, branched chain or cyclic alkoxy group such as a methoxy group, an ethoxy group, a propoxy group, an isopropoxy group, a butoxy group, a sec-butoxy group, a tert-butoxy group, a pentyloxy group, a 2,2-dimethylpropoxy group, a hexyloxy group, a cyclohexyloxy group, a heptyloxy group, an octyloxy group, a nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a nonadecyloxy group and an icosyloxy group, and a C1-C6 alkoxy group is preferable and a C1-C6 linear or branched chain alkoxy group is more preferable.

The hydrocarbon group and the alkoxy group may be substituted with at least one group selected from the group consisting of a fluorine atom, a C1-C20 alkoxy group, a C6-C20 aryl group, a C6-C20 aryloxy group, a C2-C20 acyl group and a C6-C20 arylsulfonyl group.

Examples of the C1-C20 alkoxy group include the same as described above. Examples of the C6-C20 aryl group include a phenyl group, a 4-methylphenyl group, a 2-methylphenyl group, a 1-naphthyl group, a 2-naphthyl group, a 3-phenanthryl group and a 2-anthryl group. Examples of the C6-C20 aryloxy group include those composed of the above-mentioned C6-C20 aryl group and an oxygen atom such as a phenoxy group, a 4-methylphenoxy group, a 2-methylphenoxy group, a 1-naphthyloxy group, a 2-naphthyloxy group, a 3-phenanthryloxy group and a 2-anthryloxy group.

Examples of the C2-C20 acyl group include a C2-C20 aliphatic or aromatic acyl group such as an acetyl group, a propionyl group, a butyryl group, an isobutyryl group, a benzoyl group, a 1-naphthoyl group and a 2-naphthoyl group. Examples of the C6-C20 arylsulfonyl group include a phenylsulfonyl group and a p-toluenesulfonyl group.

As (c1), a group represented by the formula (10) wherein $A^1$ is an isopropoxy group, a 2,2-dimethypropoxy group, a cyclohexyloxy group, a diethylamino group or a dodecylamino group is preferable, and a group represented by the formula (10) wherein $A^1$ is an isopropoxy group, a 2,2-dimethylpropoxy group or a cyclohexyloxy group is more preferable.

Examples of the C1-C20 alkoxy group, the C6-C20 aryl group and the C6-C20 aryloxy group in (g1) include the same as described above, respectively. Examples of the C1-C20 alkyl group include a methyl group, an ethyl group, a propyl group, an isopropyl group, a butyl group, an isobutyl group, a sec-butyl group, a tert-butyl group, a pentyl group, a 2,2-dimethylpropyl group, a cyclopentyl group, a hexyl group, a cyclohexyl group, a heptyl group, a 2-methylpentyl group, an octyl group, a 2-ethylhexyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group and an icosyl group.

As (g1), a C1-C20 unsubstituted alkyl group, a C1-C20 alkyl group substituted with one or more fluorine atoms such as a trifluoromethyl group, a C1-C20 alkyl group substituted with a C1-C20 alkoxy group such as a methoxymethyl group and a C1-C20 alkyl group substituted with a cyano group such as a cyanomethyl group are preferable.

Examples of the C1-C20 alkoxy group, the C6-C20 aryl group, the C6-C20 aryloxy group and the C2-C20 acyl group in (h1) include the same as described above, respectively.

As (h1), a C2-C20 unsubstituted acyl group and a C2-C20 acyl group substituted with a C6-C20 aryloxy group such as a phenoxybenzoyl group are preferable.

The above-mentioned (c1), (g1) and (h1) may be bonded to a carbon atom other than the neighboring carbon atoms to the carbon atom to which the above-mentioned leaving group is bonded.

The above-mentioned (c1), (g1) and (h1) are groups uninvolved in the reaction.

Alternatively, the above-mentioned aromatic ring may have a group uninvolved in the reaction other than the above-mentioned (c1), (g1) and (h1).

Examples of the group uninvolved in the reaction other than the above-mentioned (c1), (g1) and (h1) include the following (a1), (b1), (d1), (e1) and (f1).

(a1) a fluorine atom;
(b1) a cyano group;
(d1) a C1-C20 alkoxy group which may be substituted with at least one substituent selected from the group consisting of a fluorine atom, a cyano group, a C1-C20 alkoxy group, a C6-C20 aryl group and a C6-C20 aryloxy group;
(e1) a C6-C20 aryl group which may be substituted with at least one substituent selected from the group consisting of a fluorine atom, a cyano group, a C1-C20 alkoxy group and a C6-C20 aryloxy group;
(f1) a C6-C20 aryloxy group which may be substituted with at least one substituent selected from the group consisting of a fluorine atom, a cyano group, a C1-C20 alkoxy group and a C6-C20 aryloxy group.

Examples of the C1-C20 alkoxy group, the C6-C20 aryl group and the C6-C20 aryloxy group in (d1), (e1) and (f1) include the same as described above, respectively.

As (d1), a C1-C20 unsubstituted alkoxy group and a C1-C20 alkoxy group substituted with a C1-C20 alkoxy group such as a methoxymethoxy group are preferable.

As (e1), a C6-C20 unsubstituted aryl group is preferable.

As (f1), a C6-C20 unsubstituted aryloxy group is preferable.

As the group uninvolved in the reaction, the above-mentioned (c1), (d1), (g1) and (h1) are preferable.

As the leaving group, a chlorine atom and a bromine atom are more preferable.

Examples of the aromatic compound (A) include chlorobenzene, bromobenzene, iodobenzene, 4-chlorofluorobenzene, 3-chlorofluorobenzene, 2-chlorofluorobenzene, 3-chlorotoluene, 3,5-dimethylchlorobenzene, 4-ethylchlorobenzene, 3-propylchlorobenzene, 4-isopropylchlorobenzene, 5-butylchlorobenzene, 3-isobutylchlorobenzene, 3-sec-butylchlorobenzene, 4-tert-butylchlorobenzene, 5-(2,2-dimethylpropyl)chlorobenzene, 4-hexylchlorobenzene, 4-cyclohexylchlorobenzene, 4-benzylchlorobenzene, 4-chlorobenzonitrile, 4-chlorobiphenyl, 2-chlorobiphenyl, 4-chlorobenzotrifluoride, 3-chlorobenzotrifluoride, (4-chlorophenyl)acetonitrile, 3-chloroanisole, 4-chloroanisole, 2,3-dimethoxychlorobenzene, 2,4-dimethoxychlorobenzene, 2,5-dimethoxychlorobenzene, 2-ethoxychlorobenzene, 3-propoxychlorobenzene, 4-isopropoxychlorobenzene, 5-butoxychlorobenzene, 4-tert-butoxychlorobenzene, 4-phenoxychlorobenzene, 4-benzyloxychlorobenzene, 4-(methoxymethyl)chlorobenzene, 4-(butoxymethyl)chlorobenzene, 4-(methoxymethoxy)chlorobenzene, 4-(benzyloxymethoxy)chlorobenzene, 4-(2-butoxyethoxy)chlorobenzene, 4-chloroacetophenone, 3-chloroacetophenone, 4-chloropropiophenone, 1-(4-chlorophenyl)-2,2-dimethylpropanone, (4-chlorobenzoyl)cyclohexane, 4-chlorobenzophenone, p-chlorobenzalacetone, 1-chloro-4-(phenylsulfonyl)benzene, 4-chlorophenyl p-tolyl sulfone, methyl 4-chlorobenzenesulfonate, methyl 3-chlorobenzenesulfonate, ethyl 3-chlorobenzenesulfonate, ethyl 4-chlorobenzenesulfonate, 2,2-dimethylpropyl 4-chlorobenzoate, 2,2-dimethylpropyl 3-chlorobenzoate, N,N-dimethyl-4-chlorobenzenesulfonamide, N,N-dimethyl-3-chlorobenzenesulfonamide, N,N-diethyl-3-chlorobenzenesulfonamide, N,N-diethyl-4-chlorobenzenesulfonamide, 1-chloronaphthalene, 2-bromothiophene, 5-bromo-3-hexylthiophene, 2-bromo-4-dodecylthiophene, 5-bromo-2,2'-bithiophene, 5-bromo-3-cyclohexylthiophene, 2-chloro-4-octylthiophene, 5-chloro-3-phenylthiophene, 1-methyl-3-chloropyrrole, 1-hexyl-3-bromopyrrole, 1-octyl-3-chloropyrrole, 2-chloropyridine, 3-chloropyridine, 5-bromopyridine, 4-methyl-2-chloropyridine, 5-methyl-2-chloropyridine, 3-hexyl-5-chloropyridine, 5-chloro-2,2'-bipyridine, 3,3'-dimethyl-5-chloro-2,2'-bipyridine, 3,3'-dioctyl-5-bromo-2,2'-bipyridine, 1,3-dichlorobenzene, 1,4-dibromobenzene, 1,4-diiodobenzene, 3,5-dichlorotoluene, 3,5-dibromotoluene, 3,5-diiodotoluene, 3,4-dibromotoluene, 2,5-dichloroanisole, 2,4-dichloroanisole, 3,5-dichloroanisole, 2,5-dibromoanisole, 2,4-dibromoanisole, 2,5-dibromoanisole, 3,5-diiodoanisole, 1,3-dichloro-4-acetoxybenzene, 1,4-dibromo-3-acetoxybenzene, 1,3-diiodo-4-acetoxybenzene, 1,4-dichloro-2-phenoxybenzene, 1,5-dichloro-3-phenoxybenzene, 1,4-dibromo-2-phenoxybenzene, 1,5-dichloro-3-phenoxybenzene, 3,5-dichloro-4'-phenoxybenzophenone, 1,3-dibromo-5-ethylbenzene, 1,4-dibromo-2-methoxybenzene, dimethyl 2,5-dibromoterephthalate, 1,4-dibromonaphthalene, 1,1'-dibromo-4,4'-biphenyl, 1,4-dibromo-2,5-dihexyloxybenzene, 1-bromo-4-chlorobenzene, 3-bromo-5-chlorotoluene, 3-bromo-5-chloro-2-propylbenzene, 3,5-dibromo-4'-phenoxybenzophenone, 2,5-dibromothiophene, 5,5'-dibromo-2,2'-bithiophene, 2,5-dichloro-3-phenylthiophene, 2,5-dichloropyridine, 3,5-dichloropyridine, 2,5-dibromopyridine, 4-methyl-2,6-dichloropyridine, 4-hexyl-2,6-dichloropyridine, 5,5'-dichloro-2,2'-bipyridine, 3,3'-dimethyl-5,5'-dichloro-2,2'-bipyridine, 3,3'-dioctyl-5,5'-dibromo-2,2'-bipyridine, 2,7-dibromo-9,9-dihexyl-9H-fluorene, 2,7-dibromo-9,9-dioctyl-9H-fluorene, 2,7-dibromo-9,9-didodecyl-9H-fluorene, 2,7-dichloro-9,9-dihexyl-9H-fluorene, 2,7-dichloro-9,9-dioctyl-9H-fluorene, 2,7-dichloro-9,9-didodecyl-9H-fluorene, 2-bromo-7-chloro-9,9-dihexyl-9H-fluorene, 2-bromo-7-chloro-9,9-dioctyl-9H-fluorene 2-bromo-7-chloro-9,9-didodecyl-9H-fluorene, 1,2-ethylene glycol bis(p-chlorobenzoate), 1,2-ethylene glycol bis(m-chlorobenzoate), 1,4-butanediol bis(p-chlorobenzoate), 1,4-butanediol bis(m-chlorobenzoate), 1,7-heptanediol bis(p-chlorobenzoate) and 1,7-heptanediol bis(m-chlorobenzoate).

As the aromatic compound (A), a commercially available one may be used, and one produced according to the known method may be used.

As the aromatic compound (A), an aromatic compound represented by the following formula (5)

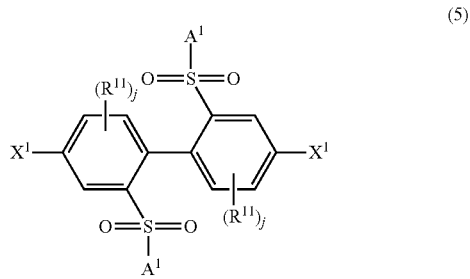

wherein $A^1$ is the same as defined above, $R^{11}$ is independently in each occurrence a fluorine atom, a C1-C20 alkyl group, a C1-C20 alkoxy group, a C6-C20 aryl group, a C6-C20 aryloxy group, a C2-C20 acyl group or a cyano group, and the above-mentioned C1-C20 alkyl group, the above-mentioned C1-C20 alkoxy group, the above-mentioned C6-C20 aryl group, the above-mentioned C6-C20 aryloxy group and the above-mentioned C2-C20 acyl group may be substituted with at least one substituent selected from the group consisting of a fluorine atom, a cyano group, a C1-C20 alkoxy group, a C6-C20 aryl group and a C6-C20 aryloxy group, and $R^{11}$s being bonded to the neighboring two carbon atoms may be bonded to form a ring, with the proviso that when $R^{11}$ is a C1-C20 alkyl group or a C2-C20 acyl group, $R^{11}$ is bonded to a carbon atom other than the neighboring carbon atoms to the carbon atom to which $X^1$ is bonded, $X^1$ represents a chlorine atom, a bromine atom or an iodine atom, and j represents an integer of 0 to 3, is also preferable.

Examples of the C1-C20 alkyl group, the C1-C20 alkoxy group, the C6-C20 aryl group, the C6-C20 aryloxy group and the C2-C20 acyl group in $R^{11}$ include the same as described above, respectively. As $R^{11}$, a C1-C20 unsubstituted alkyl group and a C1-C20 unsubstituted alkoxy group are preferable.

As $X^1$, a chlorine atom and a bromine atom are preferable, j is preferably 0.

Examples of the aromatic compound represented by the formula (5) include dimethyl 4,4'-dichlorobiphenyl-2,2'-disulfonate, diethyl 4,4'-dichlorobiphenyl-2,2'-disulfonate, dipropyl 4,4'-dichlorobiphenyl-2,2'-disulfonate, diisopropyl 4,4'-dichlorobiphenyl-2,2'-disulfonate, dibutyl 4,4'-dichlorobiphenyl-2,2'-disulfonate, diisobutyl 4,4'-dichlorobiphenyl-2,2'-disulfonate, di(2,2-dimethylpropyl) 4,4'-dichlorobiphenyl-2,2'-disulfonate, dicyclohexyl 4,4'-dichlorobiphenyl-2,2'-disulfonate, dioctyl 4,4'-dichlorobiphenyl-2,2'-disulfonate, dipentadecyl 4,4'-dichlorobiphenyl-2,2'-disulfonate, diicosyl 4,4'-dichlorobiphenyl-2,2'-disulfonate, N,N-dimethyl-4,4'-dichlorobiphenyl-2,2'-disulfonamide, N,N-diethyl-4,4'-dichlorobiphenyl-2,2'-disulfonamide, N,N-dipropyl-4,4'-dichlorobiphenyl-2,2'-disulfonamide, N,N-diisopropyl-4,4'-dichlorobiphenyl-2,2'-disulfonamide, N,N-dibutyl-4,4'-dichlorobiphenyl-2,2'-disulfonamide, N,N-diisobutyl-4,4'-dichlorobiphenyl-2,2'-disulfonamide, N,N-di(2,2-dimethylpropyl)-4,4'-dichlorobiphenyl-2,2'-disulfonamide, N,N-dioctyl-4,4'-dichlorobiphenyl-2,2'-disulfonamide, N,N-didodecyl-4,4'-dichlorobiphenyl-2,2'-disulfonamide, N,N-diicosyl-4,4'-dichlorobiphenyl-2,2'-disulfonamide, N,N-diphenyl-4,4'-dichlorobiphenyl-2,2'-disulfonamide, di(2,2-dimethylpropyl) 6,6'-dimethyl-4,4'-dichlorobiphenyl-2,2'-disulfonate, di(2,2-dimethylpropyl) 3,3'-dimethoxy-4,4'-dichlorobiphenyl-2,2'-disulfonate, di(2,2-dimethylpropyl) 5,5'-dimethoxy-4,4'-dichlorobiphenyl-2,2'-disulfonate, di(2,2-dimethylpropyl) 6,6'-dimethoxy-4,4'-dichlorobiphenyl-2,2'-disulfonate, di(2,2-dimethylpropyl) 3,3'-diphenyl-4,4'-dichlorobiphenyl-2,2'-disulfonate, dimethyl 4,4'-dibromobiphenyl-2,2'-disulfonate, diethyl 4,4'-dibromobiphenyl-2,2'-disulfonate, dipropyl 4,4'-dibromobiphenyl-2,2'-disulfonate, diisopropyl 4,4'-dibromobiphenyl-2,2'-disulfonate, dibutyl 4,4'-dibromobiphenyl-2,2'-disulfonate, diisobutyl 4,4'-dibromobiphenyl-2,2'-disulfonate, di(2,2-dimethylpropyl) 4,4'-dibromobiphenyl-2,2'-disulfonate, dicyclohexyl 4,4'-dibromobiphenyl-2,2'-disulfonate, dioctyl 4,4'-dibromobiphenyl-2,2'-disulfonate, dipentadecyl 4,4'-dibromobiphenyl-2,2'-disulfonate, diicosyl 4,4'-dibromobiphenyl-2,2'-disulfonate, N,N-dimethyl-4,4'-dibromobiphenyl-2,2'-disulfonamide, N,N-diethyl-4,4'-dibromobiphenyl-2,2'-disulfonamide, N,N-dipropyl-4,4'-dibromobiphenyl-2,2'-disulfonamide, N,N-diisopropyl-4,4'-dibromobiphenyl-2,2'-disulfonamide, N,N-dibutyl-4,4'-dibromobiphenyl-2,2'-disulfonamide, N,N-diisobutyl-4,4'-dibromobiphenyl-2,2'-disulfonamide, N,N-di(2,2-dimethylpropyl)-4,4'-dibromobiphenyl-2,2'-disulfonamide, N,N-dioctyl-4,4'-dibromobiphenyl-2,2'-disulfonamide, N,N-didodecyl-4,4'-dibromobiphenyl-2,2'-disulfonamide, N,N-diicosyl-4,4'-dibromobiphenyl-2,2'-disulfonamide and N,N-diphenyl-4,4'-dibromobiphenyl-2,2'-disulfonamide.

Among them, preferred are diisopropyl 4,4'-dichlorobiphenyl-2,2'-disulfonate, di(2,2-dimethylpropyl) 4,4'-dichlorobiphenyl-2,2'-disulfonate, diisopropyl 4,4'-dibromobiphenyl-2,2'-disulfonate and di(2,2-dimethylpropyl) 4,4'-dibromobiphenyl-2,2'-disulfonate.

The aromatic compound represented by the formula (5) can be produced, for example, according to the method described in WO 2007/102235.

The aromatic compound (B) is an aromatic compound which is structurally different from the above-mentioned aromatic compound (A) and in which one or two leaving groups selected from the group consisting of an iodine atom, a bromine atom and a chlorine atom are bonded to an aromatic ring and which does not have the above-mentioned (c1), (g1) and (h1) at the neighboring carbon atom to the carbon atom to which the leaving group is bonded.

Examples of the aromatic compound (B) include the same as the aromatic compound (A).

Alternatively, Specific examples of the aromatic compound (B) also include an aromatic compound represented by the formula (6)

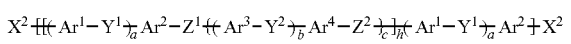

wherein a, b and c are the same or different and represent 0 or 1, and h represents an integer of 5 or more, Ar¹, Ar², Ar³ and Ar⁴ independently each represent a divalent aromatic group, and the divalent aromatic group may be substituted with at least one substituent selected from the group consisting of the following (a2) to (e2):

(a2) a C1-C20 alkyl group which may be substituted with at least one substituent selected from the group consisting of a fluorine atom, a cyano group, a C1-C20 alkoxy group, a C6-C20 aryl group and a C6-C20 aryloxy group;

(b2) a C1-C20 alkoxy group which may be substituted with at least one substituent selected from the group consisting of a fluorine atom, a cyano group, a C1-C20 alkoxy group, a C6-C20 aryl group and a C6-C20 aryloxy group;

(c2) a C6-C20 aryl group which may be substituted with at least one substituent selected from the group consisting of a fluorine atom, a cyano group, a C1-C20 alkoxy group and a C6-C10 aryloxy group;

(d2) a C6-C20 aryloxy group which may be substituted with at least one substituent selected from the group consisting of a fluorine atom, a cyano group, a C1-C20 alkoxy group and a C6-C20 aryloxy group; and (e2) a C2-C20 acyl group which may be substituted with at least one substituent selected from the group consisting of a fluorine atom, a cyano group, a C1-C20 alkoxy group, a C6-C20 aryl group and a C6-C20 aryloxy group, with the proviso that (a2) and (e2) are not bonded to the neighboring carbon atoms to the carbon atoms of Ar¹ and Ar² to which X² is bonded, Y¹ and Y² independently each represent a single bond, —CO—, —SO₂—, —C(CH₃)₂—, —C(OF₃)₂— or a fluorene-9,9-diyl group, Z¹ and Z² independently each represent —O— or —S—, and X² represents a chlorine atom, a bromine atom or an iodine atom.

In the formula (6), h is preferably an integer of 10 or more.

Examples of the divalent aromatic group in Ar², Ar³, Ar⁴ and Ar⁵ include a divalent monocyclic aromatic group such as a 1,3-phenylene group, a 1,4-phenylene group and 4,4'-biphenyl-1,1'-diyl group; a divalent condensed aromatic group such as a naphthalene-1,3-diyl group, a naphthalene-1,4-diyl group, a naphthalene-1,5-diyl group, a naphthalene-1,6-diyl group, a naphthalene-1,7-diyl group, a naphthalene-2,6-diyl group, a naphthalene-2,7-diyl group and a 9H-fluorene-2,7-diyl group; and a divalent heteroaromatic group such as a pyridine-2,5-diyl group, a pyridine-2,6-diyl group, a quinoxaline-2,6-diyl group, a thiophene-2,5-diyl group, 2,2'-bithiophene-5,5'-diyl group, a pyrrole-2,5-diyl group, a 2,2'-bipyridine-5,5'-diyl group, a pyrimidine-2,5-diyl group, a quinoline-5,8-diyl group, a quinoline-2,6-diyl group, an isoquinoline-1,4-diyl group, an isoquinoline-5,8-diyl group, 2,1,3-benzothiadiazole-4,7-diyl group, a benzimidazole-4,7-diyl group, a quinoxaline-5,8-diyl group and a quinoxaline-2,6-diyl group. Among them, preferred are the divalent monocyclic aromatic group and the divalent condensed aromatic group, and more preferred are a 1,4-phenylene group, a naphthalene-1,4-diyl group, a naphthalene-1,5-diyl group, a naphthalene-2,6-diyl group and a naphthalene-2,7-diyl group.

The divalent aromatic group may be substituted with at least one substituent selected from the group consisting of the following (a2) to (e2).

(a2) a C1-C20 alkyl group which may be substituted with at least one substituent selected from the group consisting of a fluorine atom, a cyano group, a C1-C20 alkoxy group, a C6-C20 aryl group and a C6-C20 aryloxy group;

(b2) a C1-C20 alkoxy group which may be substituted with at least one substituent selected from the group consisting of a fluorine atom, a cyano group, a C1-C20 alkoxy group, a C6-C20 aryl group and a C6-C20 aryloxy group;

(c2) a C6-C20 aryl group which may be substituted with at least one substituent selected from the group consisting of a fluorine atom, a cyano group, a C1-C20 alkoxy group and a C6-C10 aryloxy group;

(d2) a C6-C20 aryloxy group which may be substituted with at least one substituent selected from the group consisting of a fluorine atom, a cyano group, a C1-C20 alkoxy group and a C6-C20 aryloxy group; and (e2) a C2-C20 acyl group which may be substituted with at least one substituent selected from the group consisting of a fluorine atom, a cyano group, a C1-C20 alkoxy group, a C6-C20 aryl group and a C6-C20 aryloxy group.

Examples of the C1-C20 alkoxy group, the C6-C20 aryl group, the C6-C20 aryloxy group, the C1-C20 alkyl group and the C2-C20 acyl group in (a2) to (e2) include the same as described above.

Examples of (a2) include the same as the above-mentioned (g1). Examples of (b2) include the same as the above-mentioned (d1). Examples of (c2) include the same as the above-mentioned (e1). Examples of (d2) include the same as the above-mentioned (f1). Examples of (e2) include the same as the above-mentioned (h1).

To the carbon atoms of Ar¹ and Ar² to which X² is bonded, (a2) and (e2) are not bonded to the neighboring carbon atoms.

As X², a chlorine atom and a bromine atom are preferable.

Specific examples of the aromatic compound represented by the formula (6) include the compounds represented by the following and compounds wherein both terminal chlorine atoms in the compounds represented by the following are replaced by bromine atoms. In the following formulae, h represents the same meanings as the above.

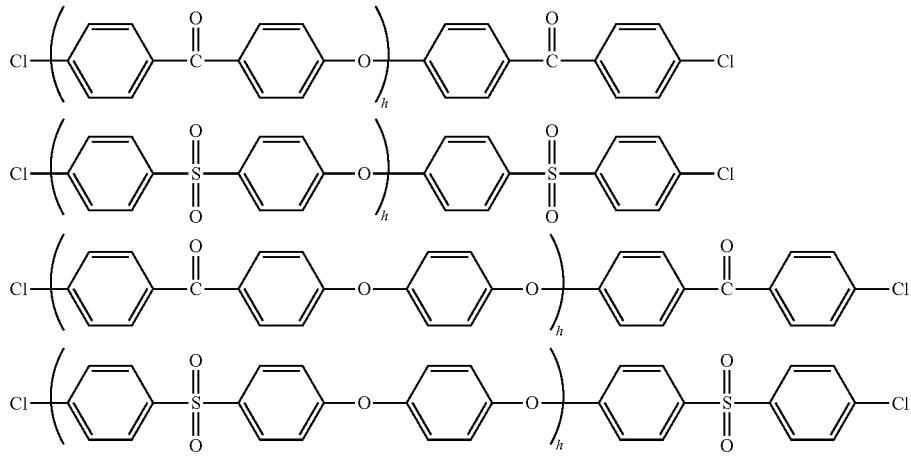

-continued
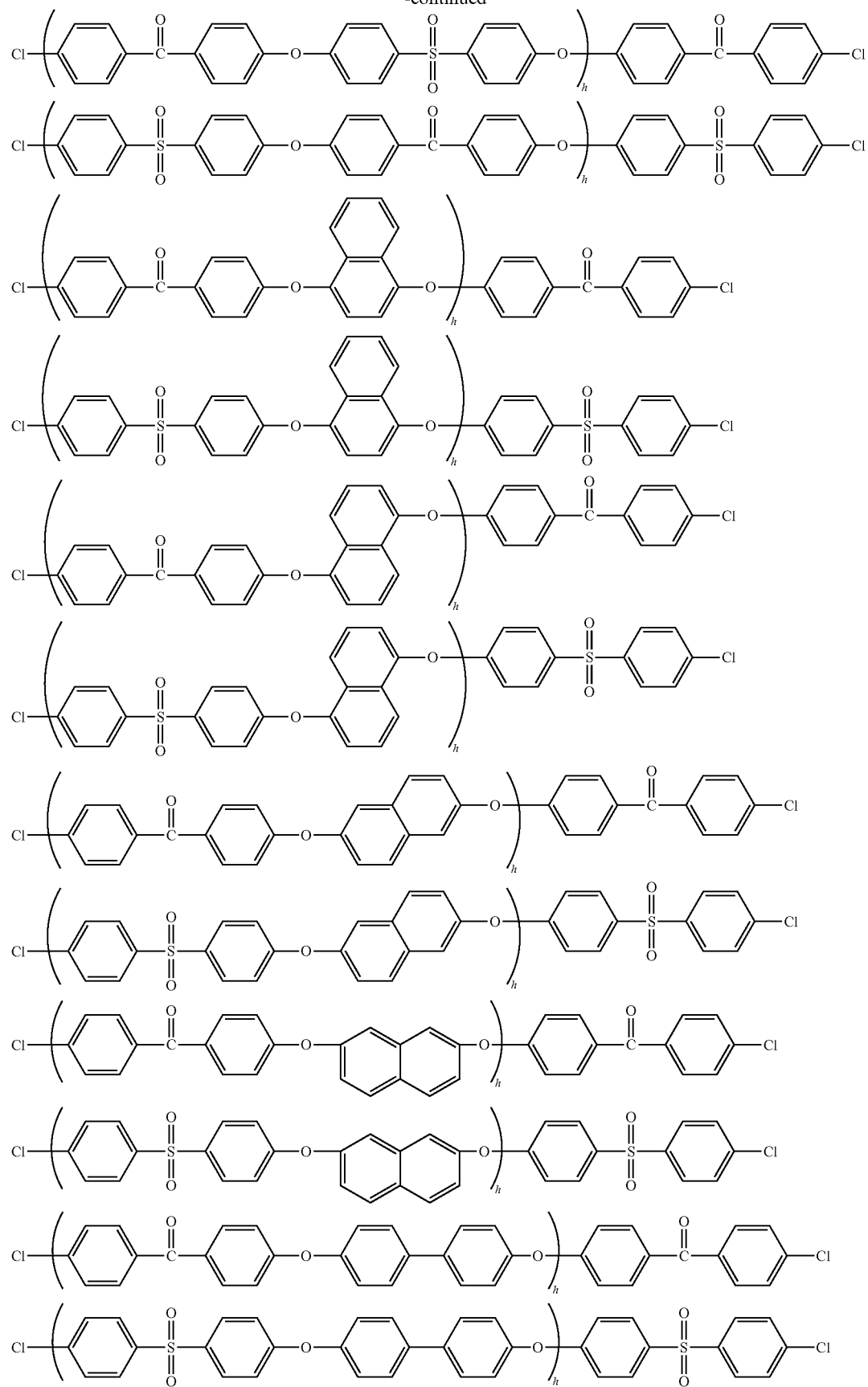

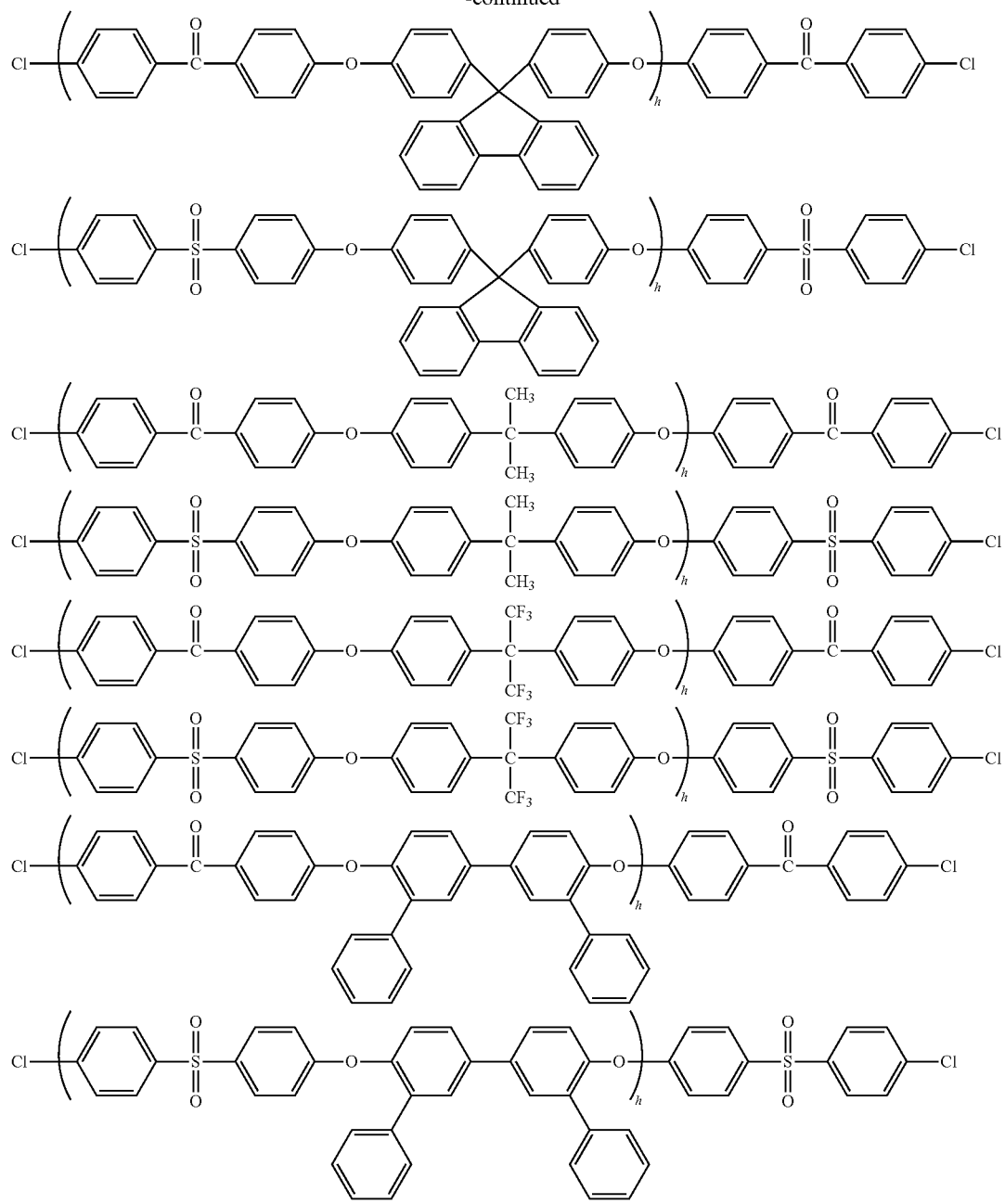

As the aromatic compound represented by the formula (6), one produced according to known methods such as JP Patent No. 2,745,727 may be used and a commercially available one may be used. Examples of the commercially available one include SUMIKA EXCEL PES manufactured by Sumitomo Chemical Company, Limited.

As the aromatic compound represented by the formula (6), one having a weight average molecular weight equivalent to polystyrene of 2,000 or more is preferably used, and one having a weight average molecular weight equivalent to polystyrene of 3,000 or more is more preferable.

The present invention is a method for manufacturing a conjugated aromatic compound comprising reacting the aromatic compound (A) with the aromatic compound (A) having the same structure as that of the above-mentioned aromatic compound (A) or the aromatic compound (B) being structurally different from the above-mentioned aromatic compound (A) in the presence of (i) a nickel compound, (ii) a metal reducing agent, (iii) at least one ligand (L1) selected from the group consisting of a 2,2'-bipyridine compound having at least one electron-withdrawing group and having no substituent at 3-, 6-, 3'- and 6'-position, and a 1,10-phenanthroline compound having at least one electron-withdrawing group and having no substituent at 2- and 9-position, and (iv) at least one ligand (L2) selected from the group consisting of a 2,2'-bipyridine compound having at least one electron-releasing group and having no substituent at 3-, 6-, 3'- and 6'-positions, and a 1,10-phenanthroline compound having at least one electron-releasing group and having no substituent at 2- and 9-positions.

Specific examples of cases where the aromatic compound (A) is reacted with the aromatic compound (A) having the same structure as that of the above-mentioned aromatic compound (A) include a case where the aromatic compound represented by the formula (5) is used as the aromatic compound (A).

Specific examples of cases where the aromatic compound (A) is reacted with the aromatic compound (B) being structurally different from the above-mentioned aromatic compound (A) include a case where the aromatic compound represented by the formula (5) is used as the aromatic compound (A) and the aromatic compound represented by the formula (5) and being structurally different from the above-mentioned aromatic compound (A) is used as the aromatic compound (B); and a case where the aromatic compound represented by the formula (5) is used as the aromatic compound (A) and the aromatic compound represented by the formula (6) is used as the aromatic compound (B).

When the aromatic compound (A) is reacted with the aromatic compound (B) being structurally different from the above-mentioned aromatic compound (A), the content of the repeating unit derived from the aromatic compound (A) and the content of the repeating unit derived from the aromatic compound (B) in the conjugated aromatic compound obtained can be adjusted, respectively, by adjusting the used amount of the aromatic compound (A) and the used amount of the aromatic compound (B) respectively.

Examples of the nickel compound include a zero-valent nickel compound such as bis(cyclooctadiene)nickel(0) and tetrakis(triphenylphosphine) nickel(0); and a divalent nickel compound such as a nickel halide (for example, nickel fluoride, nickel chloride, nickel bromide, nickel iodide and the like), a nickel carboxylate (for example, nickel formate, nickel acetate and the like), nickel sulfate, nickel carbonate, nickel nitrate, nickel acetylacetonate and (dimethoxyethane) nickel chloride, and bis(cyclooctadiene)nickel(0) and a nickel halide are preferable.

While the used amount of the nickel compound may be a catalytic amount, and when the used amount thereof is too small, the yield of a conjugated aromatic compound tends to be low or a conjugated aromatic compound having a small molecular weight tends to be obtained, and when the used amount thereof is too much, the isolation procedure of an conjugated aromatic compound after completion of reaction tends to be cumbersome, and therefore, the used amount of the nickel compound is usually 0.001 to 0.8 mole and preferably 0.01 to 0.3 mole per 1 mole of all of the aromatic compounds involved in the reaction.

"Metal reducing agent" means a metal capable of reducing divalent nickel to zero-valent nickel. Specific examples thereof include zinc, magnesium, manganese, aluminum and sodium, and zinc, magnesium and manganese are preferable, and zinc is more preferable. Usually, a commercially available metal reducing agent is used. Alternatively, powdery or chip-type metal reducing agent is usually used. The used amount of the metal reducing agent is usually 1 mole or more per 1 mole of all of the aromatic compounds involved in the reaction. While the upper limit thereof is not limited, when the used amount thereof is too much, the isolation procedure of an conjugated aromatic compound after completion of reaction tends to be cumbersome and it easily becomes to be economically disadvantageous, and therefore, it is practically 10 moles or less and preferably 5 moles or less.

The ligand (L1) is at least one selected from the group consisting of a 2,2'-bipyridine compound having at least one electron-withdrawing group and having no substituent at 3-, 6-, 3'- and 6'-positions, and a 1,10-phenanthroline compound having at least one electron-withdrawing group and having no substituent at 2- and 9-positions.

"Electron-withdrawing group" means a substituent wherein the value of σ defined by Hammett formula described in Chemical Reviews 1991, 91, 165-195 is positive.

Specific examples thereof include a fluorine atom, a C1-C20 fluorinated alkyl group, a C2-C20 alkoxycarbonyl group, a C2-C20 acyl group, a cyano group and a nitro group. Among them, preferred are a fluorine atom, a C1-C20 fluorinated alkyl group and a C2-C20 alkoxycarbonyl group.

Examples of the C1-C20 fluorinated alkyl group include a monofluoromethyl group, a difluoromethyl group, a trifluoromethyl group, a 2,2,2-trifluoroethyl group, a pentafluoroethyl group, a perfluoropropyl group and a perfluoroisopropyl group, and a trifluoromethyl group is preferable.

Examples of the C2-C20 alkoxycarbonyl group include a methoxycarbonyl group, an ethoxycarbonyl group, a propoxycarbonyl group and an isopropoxycarbonyl group, and a methoxycarbonyl group is preferable.

Examples of the C2-C20 acyl group include a C2-C20 aliphatic or aromatic acyl group such as an acetyl group, a propionyl group, a butyryl group, an isobutyryl group, a benzoyl group, a 1-naphthoyl group and a 2-naphthoyl group.

The 2,2'-bipyridine compound in the ligand (L1) may be a 2,2'-bipyridine compound having at least one electron-withdrawing group and having no substituent at 3-, 6-, 3'- and 6'-positions, and may have a group other than the electron-withdrawing group at a position other than 3-, 6-, 3'- and 6'-positions.

The 1,10-phenanthroline compound in the ligand (L1) may be a 1,10-phenanthroline compound having at least one electron-withdrawing group and having no substituent at 2- and 9-positions, and may have a group other than the electron-withdrawing group at a position other than 2- and 9-positions.

The ligand (L1) preferably has at least two electron-withdrawing groups.

When the ligand (L1) is a 2,2'-bipyridine compound, each of two pyridine rings has preferably one electron-withdrawing group.

When the ligand (L1) is a 1,10-phenanthroline compound, each of rings containing a nitrogen atom has preferably one electron-withdrawing group.

As the ligand (L1), a 2,2'-bipyridine compound having at least one electron-withdrawing group and having no substituent at 3-, 6-, 3'- and 6'-positions is preferable.

As the 2,2'-bipyridine compound having at least two electron-withdrawing groups and having no substituent at 3-, 6-, 3'- and 6'-positions, a bipyridine compound represented by the formula (1)

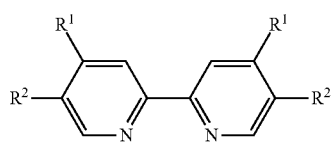

wherein $R^1$ and $R^2$ independently each represent a hydrogen atom or an electron-withdrawing group, with the proviso that $R^1$ and $R^2$ are not hydrogen atoms simultaneously, is preferable.

As the 1,10-phenanthroline compound having at least two electron-withdrawing groups and having no substituent at 2- and 9-positions, a phenanthroline compound represented by the formula (2)

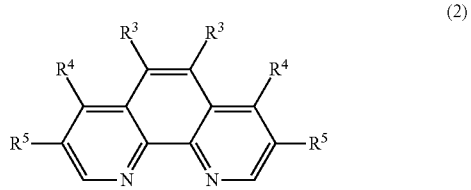

(2)

wherein $R^3$, $R^4$ and $R^5$ independently each represent a hydrogen atom or an electron-withdrawing group, with the proviso that $R^3$, $R^4$ and $R^5$ are not hydrogen atoms simultaneously, is preferable.

As the ligand (L1), the 2,2'-bipyridine compound represented by the formula (1) is more preferable.

Examples of the 2,2'-bipyridine compound represented by the formula (1) include 4,4'-difluoro-2,2'-bipyridine, 5,5'-difluoro-2,2'-bipyridine, 4,4'-bis(trifluoromethyl)-2,2'-bipyridine, 5,5'-bis(trifluoromethyl)-2,2'-bipyridine, 4,4'-bis(methoxycarbonyl)-2,2'-bipyridine, 5,5'-bis(methoxycarbonyl)-2,2'-bipyridine, 4,4'-bis(ethoxycarbonyl)-2,2'-bipyridine and 5,5'-bis(ethoxycarbonyl)-2,2'-bipyridine.

Examples of the 1,10-phenanthroline compound represented by the formula (2) include 4,7-dichloro-1,10-phenanthroline.

As the ligand (L1), two or more 2,2'-bipyridine compound may be used, and two or more 1,10-phenanthroline compound may be used.

As the ligand (L1), a commercially available one may be used, and one produced according to known methods such as Bull. Chem. Soc. Jpn., 63, 80-87 (1990) may be used.

The ligand (L2) is at least one selected from the group consisting of a 2,2'-bipyridine compound having at least one electron-releasing group and having no substituent at 3-, 6-, 3'- and 6'-positions, and a 1,10-phenanthroline compound having at least one electron-releasing group and having no substituent at 2- and 9-positions.

"Electron-releasing group" means a substituent wherein the value of σ defined by Hammett formula described in Chemical Reviews 1991, 91, 165-195 is negative.

Specific examples thereof include a C1-C20 alkyl group, a C1-C20 alkoxy group, a C6-C20 aryl group and a C1-C20 dialkylamino group. Among them, preferred are a C1-C20 alkyl group and a C1-C20 alkoxy group.

Examples of the C1-C20 alkyl group include a methyl group, an ethyl group, a propyl group, an isopropyl group, a butyl group, an isobutyl group, a sec-butyl group, a tert-butyl group, a pentyl group, a 2,2-dimethylpropyl group, a cyclopentyl group, a hexyl group, a cyclohexyl group, a heptyl group, a 2-methylpentyl group, an octyl group, a 2-ethylhexyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group and an icosyl group. Preferred are a methyl group and a tert-butyl group.

Examples of the C1-C20 alkoxy group include a methoxy group, an ethoxy group, a propoxy group, an isopropoxy group, a butoxy group, a sec-butoxy group, a tert-butoxy group, a pentyloxy group, a 2,2-dimethylpropoxy group, a hexyloxy group, a cyclohexyloxy group, a heptyloxy group, an octyloxy group, a nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a nonadecyloxy group and an icosyloxy group. Preferred is a methoxy group.

Examples of the C6-C20 aryl group include a phenyl group, a 4-methylphenyl group, a 2-methylphenyl group, a 1-naphthyl group, a 2-naphthyl group, a 3-phenanthryl group and a 2-anthryl group. Preferred is a phenyl group.

Examples of the C1-C20 dialkylamino group include a dimethylamino group, a diethylamino group, a dipropylamino group, a diisopropylamino group, a dibutylamino group and a di(2,2-dimethylpropyl)amino group. Preferred is a dimethylamino group.

The 2,2'-bipyridine compound in the ligand (L2) may be a 2,2'-bipyridine compound having at least one electron-releasing group and having no substituent at 3-, 6-, 3'- and 6'-positions, and may have a group other than the electron-releasing group at a position other than 3-, 6-, 3'- and 6'-positions.

The 1,10-phenanthroline compound in the ligand (L2) may be a 1,10-phenanthroline compound having at least one electron-releasing group and having no substituent at 2- and 9-positions, and may have a group other than the electron-releasing group at a position other than 2- and 9-positions.

The ligand (L2) preferably has at least two electron-releasing groups.

When the ligand (L2) is a 2,2'-bipyridine compound, each of two pyridine rings has preferably one electron-releasing group.

When the ligand (L2) is a 1,10-phenanthroline compound, each of rings containing a nitrogen atom has preferably one electron-releasing group.

As the ligand (L2), a 2,2'-bipyridine compound having at least one electron-releasing group and having no substituent at 3-, 6-, 3'- and 6'-positions is preferable.

As the 2,2'-bipyridine compound having at least two electron-releasing groups and having no substituent at 3-, 6-, 3'- and 6'-positions, a bipyridine compound represented by the formula (3)

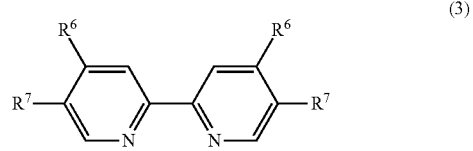

(3)

wherein $R^6$ and $R^7$ independently each represent a hydrogen atom or an electron-releasing group, with the proviso that $R^6$ and $R^7$ are not hydrogen atoms simultaneously, is preferable.

As the 1,10-phenanthroline compound having at least two electron-releasing groups and having no substituent at 2- and 9-positions, a phenanthroline compound represented by the formula (4)

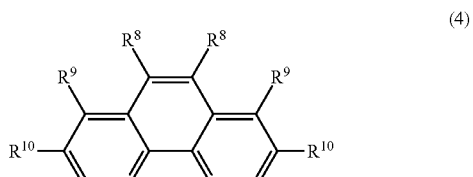

(4)

wherein $R^8$, $R^9$ and $R^{10}$ independently each represent a hydrogen atom or an electron-releasing group, with the proviso that $R^8$, $R^9$ and $R^{10}$ are not hydrogen atoms simultaneously, is preferable.

As the ligand (L2), the 2,2'-bipyridine compound represented by the formula (3) is more preferable.

Examples of the 2,2'-bipyridine compound represented by the formula (3) include 4,4'-dimethyl-2,2'-bipyridine, 4,4'-dinonyl-2,2'-bipyridine, 4,4'-dimethoxy-2,2'-bipyridine, 4,4'-diphenyl-2,2'-bipyridine, 5,5'-dimethyl-2,2'-bipyridine, 4,4',5,5'-tetramethyl-2,2'-bipyridine, 4,4'-bis(1,1-dimethylethyl)-2,2'-bipyridine and 4,4'-bis(dimethylamino)-2,2'-bipyridine.

Examples of the phenanthroline represented by the formula (4) include 3,4,7,8-tetramethyl-1,10-phenanthroline.

As the ligand (L2), two or more 2,2'-bipyridine compound may be used, and two or more 1,10-phenanthroline compound may be used.

As the ligand (L2), a commercially available one may be used, and one produced according to known methods such as Bull. Chem. Soc. Jpn., 63, 80-87 (1990) may be used.

Specific examples of the combination of the ligand (L1) and the ligand (L2) include a combination of 4,4'-difluoro-2,2'-bipyridine and 4,4'-dimethyl-2,2'-bipyridine, a combination of 4,4'-difluoro-2,2'-bipyridine and 4,4'-dinonyl-2,2'-bipyridine, a combination of 4,4'-difluoro-2,2'-bipyridine and 4,4'-dimethoxy-2,2'-bipyridine, a combination of 4,4'-difluoro-2,2'-bipyridine and 4,4'-diphenyl-2,2'-bipyridine, a combination of 4,4'-difluoro-2,2'-bipyridine and 5,5'-dimethyl-2,2'-bipyridine, a combination of 4,4'-difluoro-2,2'-bipyridine and 4,4',5,5'-tetramethyl-2,2'-bipyridine, a combination of 4,4'-difluoro-2,2'-bipyridine and 4,4'-bis(1,1-dimethylethyl)-2,2'-bipyridine, a combination of 4,4'-difluoro-2,2'-bipyridine and 4,4'-bis(dimethylamino)-2,2'-bipyridine, a combination of 5,5'-difluoro-2,2'-bipyridine and 4,4'-dimethyl-2,2'-bipyridine, a combination of 5,5'-difluoro-2,2'-bipyridine and 4,4'-dinonyl-2,2'-bipyridine, a combination of 5,5'-difluoro-2,2'-bipyridine and 4,4'-dimethoxy-2,2'-bipyridine, a combination of 5,5'-difluoro-2,2'-bipyridine and 4,4'-diphenyl-2,2'-bipyridine, a combination of 5,5'-difluoro-2,2'-bipyridine and 5,5'-dimethyl-2,2'-bipyridine, a combination of 5,5'-difluoro-2,2'-bipyridine and 4,4',5,5'-tetramethyl-2,2'-bipyridine, a combination of 5,5'-difluoro-2,2'-bipyridine and 4,4'-bis(1,1-dimethylethyl)-2,2'-bipyridine, a combination of 5,5'-difluoro-2,2'-bipyridine and 4,4'-bis(dimethylamino)-2,2'-bipyridine, a combination of 4,4'-bis(trifluoromethyl)-2,2'-bipyridine and 4,4'-dimethyl-2,2'-bipyridine, a combination of 4,4'-bis(trifluoromethyl)-2,2'-bipyridine and 4,4'-dinonyl-2,2'-bipyridine, a combination of 4,4-bis(trifluoromethyl)-2,2'-bipyridine and 4,4'-dimethoxy-2,2'-bipyridine, a combination of 4,4'-bis(trifluoromethyl)-2,2'-bipyridine and 4,4'-diphenyl-2,2'-bipyridine, a combination of 4,4'-bis(trifluoromethyl)-2,2'-bipyridine and 5,5'-dimethyl-2,2'-bipyridine, a combination of 4,4'-bis(trifluoromethyl)-2,2'-bipyridine and 4,4',5,5'-tetramethyl-2,2'-bipyridine, a combination of 4,4'-bis(trifluoromethyl)-2,2'-bipyridine and 4,4'-bis(1,1-dimethylethyl)-2,2'-bipyridine, a combination of 4,4'-bis(trifluoromethyl)-2,2'-bipyridine and 4,4'-bis(dimethylamino)-2,2'-bipyridine, a combination of 5,5'-bis(trifluoromethyl)-2,2'-bipyridine and 4,4'-dimethyl-2,2'-bipyridine, a combination of 5,5'-bis(trifluoromethyl)-2,2'-bipyridine and 4,4'-dinonyl-2,2'-bipyridine, a combination of 5,5'-bis(trifluoromethyl)-2,2'-bipyridine and 4,4'-dimethoxy-2,2'-bipyridine, a combination of 5,5'-bis(trifluoromethyl)-2,2'-bipyridine and 4,4'-diphenyl-2,2'-bipyridine, a combination of 5,5'-bis(trifluoromethyl)-2,2'-bipyridine and 5,5'-dimethyl-2,2'-bipyridine, a combination of 5,5'-bis(trifluoromethyl)-2,2'-bipyridine and 4,4',5,5'-tetramethyl-2,2'-bipyridine, a combination of 5,5'-bis(trifluoromethyl)-2,2'-bipyridine and 4,4'-bis(1,1-dimethylethyl)-2,2'-bipyridine, a combination of 5,5'-bis(trifluoromethyl)-2,2'-bipyridine and 4,4'-bis(dimethylamino)-2,2'-bipyridine, a combination of 4,4'-bis(methoxycarbonyl)-2,2'-bipyridine and 4,4'-dimethyl-2,2'-bipyridine, a combination of 4,4-bis(methoxycarbonyl)-2,2'-bipyridine and 4,4'-dinonyl-2,2'-bipyridine, a combination of 4,4'-bis(methoxycarbonyl)-2,2'-bipyridine and 4,4'-dimethoxy-2,2'-bipyridine, a combination of 4,4'-bis(methoxycarbonyl)-2,2'-bipyridine and 4,4'-diphenyl-2,2'-bipyridine, a combination of 4,4-bis(methoxycarbonyl)-2,2'-bipyridine and 5,5'-dimethyl-2,2-bipyridine, a combination of 4,4'-bis(methoxycarbonyl)-2,2'-bipyridine and 4,4',5,5'-tetramethyl-2,2'-bipyridine, a combination of 4,4'-bis(methoxycarbonyl)-2,2'-bipyridine and 4,4'-bis(1,1-dimethylethyl)-2,2'-bipyridine, a combination of 4,4'-bis(methoxycarbonyl)-2,2'-bipyridine and 4,4'-bis(dimethylamino)-2,2'-bipyridine, a combination of 5,5'-bis(methoxycarbonyl)-2,2'-bipyridine and 4,4'-dimethyl-2,2'-bipyridine, a combination of 5,5'-bis(methoxycarbonyl)-2,2'-bipyridine and 4,4'-dinonyl-2,2'-bipyridine, a combination of 5,5'-bis(methoxycarbonyl)-2,2'-bipyridine and 4,4'-dimethoxy-2,2'-bipyridine, a combination of 5,5'-bis(methoxycarbonyl)-2,2'-bipyridine and 4,4'-diphenyl-2,2'-bipyridine, a combination of 5,5'-bis(methoxycarbonyl)-2,2'-bipyridine and 5,5'-dimethyl-2,2'-bipyridine, a combination of 5,5'-bis(methoxycarbonyl)-2,2'-bipyridine and 4,4',5,5'-tetramethyl-2,2'-bipyridine, a combination of 5,5'-bis(methoxycarbonyl)-2,2'-bipyridine and 4,4'-bis(1,1-dimethylethyl)-2,2'-bipyridine, a combination of 5,5'-bis(methoxycarbonyl)-2,2'-bipyridine and 4,4'-bis(dimethylamino)-2,2'-bipyridine, a combination of 4,4'-bis(ethoxycarbonyl)-2,2'-bipyridine and 4,4'-dimethyl-2,2'-bipyridine, a combination of 4,4'-bis(ethoxycarbonyl)-2,2'-bipyridine and 4,4'-dinonyl-2,2'-bipyridine, a combination of 4,4'-bis(ethoxycarbonyl)-2,2'-bipyridine and 4,4'-dimethoxy-2,2'-bipyridine, a combination of 4,4'-bis(ethoxycarbonyl)-2,2'-bipyridine and 4,4'-diphenyl-2,2'-bipyridine, a combination of 4,4'-bis(ethoxycarbonyl)-2,2'-bipyridine and 5,5'-dimethyl-2,2'-bipyridine, a combination of 4,4'-bis(ethoxycarbonyl)-2,2'-bipyridine and 4,4',5,5'-tetramethyl-2,2'-bipyridine, a combination of 4,4'-bis(ethoxycarbonyl)-2,2'-bipyridine and 4,4'-bis(1,1-dimethylethyl)-2,2'-bipyridine, a combination of 4,4'-bis(ethoxycarbonyl)-2,2'-bipyridine and 4,4'-bis(dimethylamino)-2,2'-bipyridine, a combination of 5,5'-bis(ethoxycarbonyl)-2,2'-bipyridine and 4,4'-dimethyl-2,2'-bipyridine, a combination of 5,5'-bis(ethoxycarbonyl)-2,2'-bipyridine and 4,4'-dinonyl-2,2'-bipyridine, a combination of 5,5'-bis(ethoxycarbonyl)-2,2'-bipyridine and 4,4'-dimethoxy-2,2'-bipyridine, a combination of 5,5'-bis(ethoxycarbonyl)-2,2'-bipyridine and 4,4'-diphenyl-2,2'-bipyridine, a combination of 5,5'-bis(ethoxycarbonyl)-2,2'-bipyridine and 5,5'-dimethyl-2,2'-bipyridine, a combination of 5,5'-bis(ethoxycarbonyl)-2,2'-bipyridine and 4,4',5,5'-tetramethyl-2,2'-bipyridine, a combination of 5,5'-bis(ethoxycarbonyl)-2,2'-bipyridine and 4,4'-bis(1,1-dimethylethyl)-2,2'-bipyridine, and a combination of 5,5'-bis(ethoxycarbonyl)-2,2'-bipyridine and 4,4'-bis(dimethylamino)-2,2'-bipyridine.

The ligand (L1) and the ligand (L2) are used in an amount wherein the sum of the used amounts is usually 0.2 to 2 moles and preferably 0.5 to 1.7 moles relative to 1 mole of the nickel compound. While the used amount of each thereof is not limited, the ratio of the used amount of the ligand (L1) to the used amount of the ligand (L2) (the ligand (L1)/the ligand (L2)) is usually 0.01/0.99 to 0.99/0.01, and preferably 0.1/0.9 to 0.9/0.1. It is more preferred that the used amount of the ligand (L2) is equal to or bigger than the used amount of the ligand (L1), and it is especially preferred that the ratio of the used amount of the ligand (L1) to the used amount of the ligand (L2) (the ligand (L1)/the ligand (L2)) is 0.5/0.5 to 0.1/0.9.

The ligand (L1), the ligand (L2) and the nickel compound may be previously contacted to be used. The ligand (L1), the ligand (L2) and the nickel compound may be mixed in a solvent and the resultant mixture containing a nickel complex may be used as it is, and the nickel complex may be isolated from the mixture to be used. The ligand (L1) may be mixed with the nickel compound in a solvent and the resultant mixture containing a nickel complex may be used as it is, and the nickel complex may be isolated from the mixture to be used. The ligand (L2) may be mixed with the nickel compound in a solvent and the resultant mixture containing a nickel complex may be used as it is, and the nickel complex may be isolated from the mixture to be used. A mixture containing a nickel complex which is prepared from the ligand (L1) and the nickel compound may be mixed with the ligand (L2), and the resultant mixture containing a nickel complex may be used as it is, and the nickel complex may be isolated from the mixture to be used. A mixture containing a nickel complex which is prepared from the ligand (L2) and the nickel compound may be mixed with the ligand (L1), and the resultant mixture containing a nickel complex may be used as it is, and the nickel complex may be isolated from the mixture to be used. By change of a color of the mixture, the preparation of the nickel complex can be discerned.

The reaction of the aromatic compound (A) with the aromatic compound (A) having the same structure as that of the above-mentioned aromatic compound (A) or the aromatic compound (B) being structurally different from the above-mentioned aromatic compound (A) is usually carried out in the presence of a solvent. The solvent may be one in which the used aromatic compounds and the produced conjugated aromatic compound can be dissolved. Specific examples of the solvent include an aromatic hydrocarbon solvent such as toluene and xylene; an ether solvent such as tetrahydrofuran and 1,4-dioxane; an aprotic polar solvent such as dimethylsulfoxide, N-methyl-2-pyrrolidone, N,N-dimethylformamide, N,N-dimethylacetamide and hexamethylphosphoric triamide; and a halogenated hydrocarbon solvent such as dichloromethane and dichloroethane. These solvents may be used alone, and two or more kinds thereof may be mixed to be used. Among them, preferred are the ether solvent and the aprotic polar solvent, and more preferred are tetrahydrofuran, dimethylsulfoxide, N-methyl-2-pyrrolidone and N,N-dimethylacetamide. When the used amount of the solvent is too much, a conjugated aromatic compound having small molecular weight tends to be obtained, and when the used amount thereof is too small, the property of the reaction mixture tends to be bad, and therefore, it is usually 1 to 200 parts by weight and preferably 5 to 100 parts by weight per 1 part by weight of all of the aromatic compounds used.

The reaction is usually conducted by mixing the aromatic compounds, the nickel compound, metal reducing agent, the ligand (L1) and the ligand (L2) in an atmosphere of an inert gas such as nitrogen gas. The mixing order is not limited.

The reaction temperature is usually 0 to 250° C. and preferably 30 to 100° C. The reaction time is usually 0.5 to 48 hours.

In order to improve a reaction rate, a halogen compound may be added to the reaction system. Examples of the halogen compound include a sodium halide such as sodium fluoride, sodium chloride, sodium bromide and sodium iodide, a potassium halide such as potassium fluoride, potassium chloride, potassium bromide and potassium iodide, and a quaternary ammonium halide such as tetraethylammonium fluoride, tetraethylammonium chloride, tetraethylammonium bromide and tetraethylammonium iodide. A sodium halide is preferable, and sodium iodide is more preferable. The used amount thereof is usually 0.01 to 1 mole per 1 mole of the all of the aromatic compounds involved in the reaction, and preferably 0.05 to 0.2 mole.

The conjugated aromatic compound can be obtained by thus reaction, and "conjugated aromatic compound" means a compound having at least one aromatic ring and possessing a delocated π-electron system in a part of or all of its molecule.

When the conjugated aromatic compound produced is a polymer, for example, after completion of the reaction, the conjugated aromatic compound is precipitated by mixing a solvent in which the conjugated aromatic compound produced is not soluble or is poorly soluble with the reaction mixture, followed by separating the precipitated conjugated aromatic compound from the reaction mixture by filtration, thereby being able to isolate it. The solvent in which the conjugated aromatic compound produced is not soluble or is poorly soluble may be mixed with the reaction mixture and then an aqueous acid solution such as hydrochloric acid is added thereto followed by separating the conjugated aromatic compound precipitated from the reaction mixture by filtration. The molecular weight and structure of the conjugated aromatic compound obtained can be analyzed by a conventional means such as gel permeation chromatography and NMR. Examples of the solvent in which the produced conjugated aromatic compound is not soluble or is poorly soluble include water, methanol, ethanol and acetonitrile, and water and methanol are preferable.

When the conjugated aromatic compound produced is not a polymer, for example, after completion of the reaction, the conjugated aromatic compound produced can be isolated by concentrating the reaction mixture. The conjugated aromatic compound isolated may be further purified by a conventional purification means such as column chromatography, distillation and recrystallization.

When the aromatic compound (A) having two leaving groups is used, a polymer having a repeating unit derived from the aromatic compound (A) is obtained, and the weight-average molecular weight thereof equivalent to polystyrene is usually 1,000 to 2,000,000.

When the aromatic compound (A) having one leaving group is used and it is reacted with the aromatic compound (A) having the same structure as that of the above-mentioned aromatic compound (A), specific examples of the conjugated aromatic compound obtained include biphenyl, 4,4'-difluorobiphenyl, 3,3'-difluorobiphenyl, 2,2'-difluorobiphenyl, 3,3'-dipropylbiphenyl, 4,4'-diisopropylbiphenyl, 5,5'-dibutylbiphenyl, 3,3'-di-sec-butylbiphenyl, 4,4'-di-tert-butylbiphenyl, 5,5'-bis(2,2-dimethylpropyl)biphenyl, 4,4'-dicyclohexylbiphenyl, 4,4'-dibenzylbiphenyl, 4,4'-dicyanobiphenyl, 4,4'-bis(trifluoromethyl)biphenyl, 4,4'-bis(cyanomethyl)biphenyl, 3,3'-dimethoxybiphenyl, 4,4'-dimethoxybiphenyl, 2,2',3,3'-tetramethoxybiphenyl, 2,2',4,4'-tetramethoxybiphenyl, 2,2',5,5'-tetramethoxybiphenyl, 2,2'-diethoxybiphenyl, 3,3'-dipropoxybiphenyl, 4,4'-diisopropoxybiphenyl, 5,5'-dibutoxybiphenyl, 4,4'-di-tert-butoxybiphenyl, 4,4'-diphenoxybiphenyl, 4,4'-dibenzyloxybiphenyl, 4,4'-bis(methoxymethyl)biphenyl, 4,4'-bis(butoxymethyl)biphenyl, 4,4'-bis(methoxymethoxy)biphenyl, 4,4'-bis(benzyloxymethoxy)biphenyl, 4,4'-bis(2-butoxyethoxy)biphenyl, 4,4'-diacetylbiphenyl, 4,4'-dibenzoylbiphenyl, 4,4'-bis(phenylsulfonyl)biphenyl, dimethyl biphenyl-4,4'-disulfonate, diethyl biphenyl-4,4'-disulfonate, di(2,2-dimethylpropyl)biphenyl-4,4'-disulfonate, di(2,2-dimethylpropyl)biphenyl-3,3'-disulfonate, 1,1'-binaphthalene, 2,2'-bithiophene, 3,3'-dihexyl-5,5'-bithiophene, 1,1'-dimethyl-5,5'-bipyrrole, 2,2'-bipyridine, 3,3'-dihexyl-5,5'-bipyridine, 2,2'-bipyrimidine, 5,5'-biquinoline, 1,1'-biisoquinoline, 4,4'-bis(2,1,3-benzothiadiazole) and 7,7'-bis(benzimidazole).

When the aromatic compound (A) is reacted with the aromatic compound (A) having the same structure as that of the above-mentioned aromatic compound (A) and the aromatic compound (A) having two leaving groups is used, specific examples of the conjugated aromatic compound obtained include a conjugated aromatic compound consisting of a repeating unit represented by the following formula (21a) to (21c) and a conjugated aromatic compound consisting a repeating unit represented by the following formula (22a) to (22e).

(21a)

(21b)

(21c)

(22a)

(22b)

(22c)

(22d)

(22e)

The conjugated aromatic compound usually contains the repeating unit of 2 to 10,000, and the weight-average molecular weight thereof equivalent to polystyrene is usually 500 to 3,000,000.

When the aromatic compound (A) is reacted with the aromatic compound (A) having the same structure as that of the above-mentioned aromatic compound (A) and the aromatic compound represented by the formula (5) is used as the aromatic compound (A), specific examples of the conjugated aromatic compound obtained include a conjugated aromatic compound consisting of a repeating unit represented by the following formula (23).

(23)

The conjugated aromatic compound usually contains the repeating unit represented by the formula (23) of 2 to 10,000, and the weight-average molecular weight thereof equivalent to polystyrene is usually 1,000 to 6,000,000.

Specific examples of the repeating unit represented by the formula (23) include the repeating units represented by the following formulae (23a) to (23d).

(23a)

(23b)

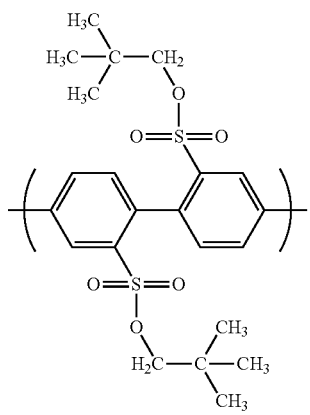

(23c)

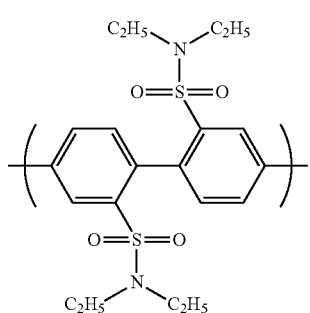

(23d)

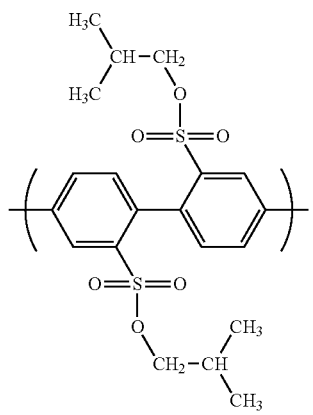

When the aromatic compound (A) having two leaving groups is used as the aromatic compound (A) and the aromatic compound represented by the formula (6) is used as the aromatic compound (B), specific examples of the conjugated aromatic compound obtained include a conjugated aromatic compound comprising a repeating unit derived from the aromatic compound (A) having two leaving groups and the segment represented by the following formula (24)

(24)

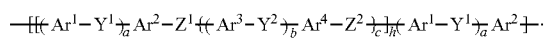

The weight-average molecular weight thereof equivalent to polystyrene is usually 3,000 to 3,000,000.

Specific examples of the segment represented by the formula (24) include the segments represented by the following formulae (24a) to (24x). Additionally, in the following formulae, h represents the same meaning as defined above and is preferably an integer of 10 or more.

(24a)

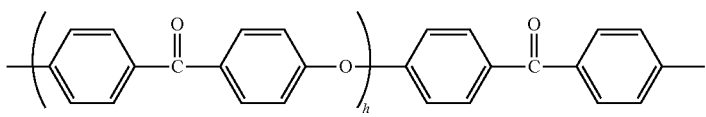

(24b)

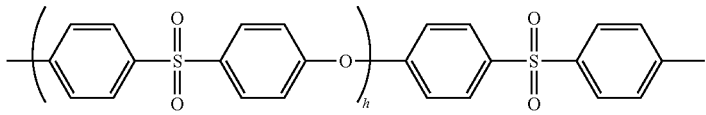

(24c)

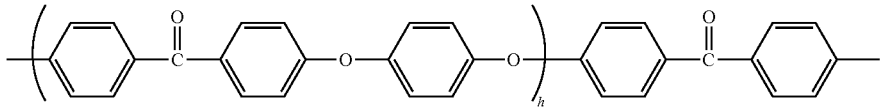

(24d)

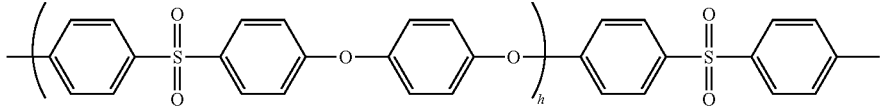

(24e)

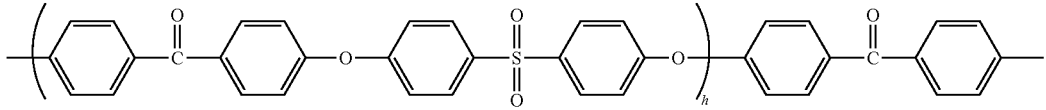

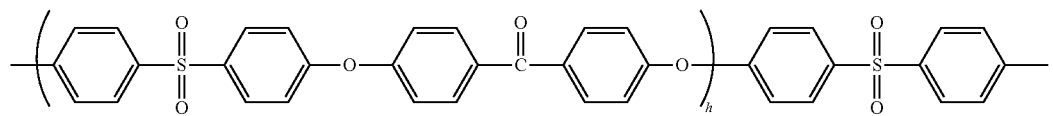
(24f)
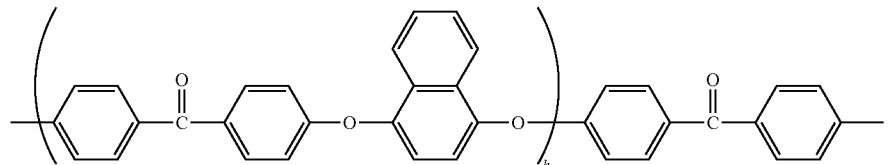
(24g)
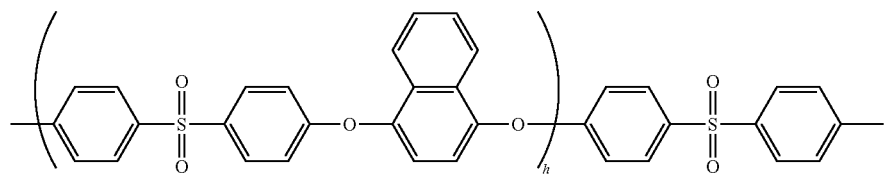
(24h)
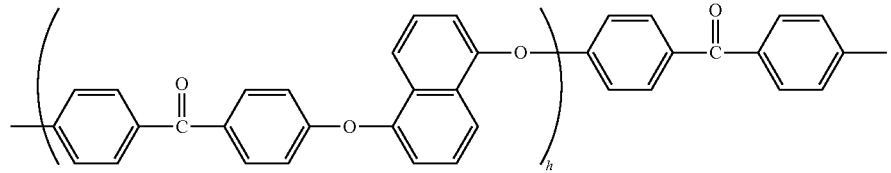
(24i)
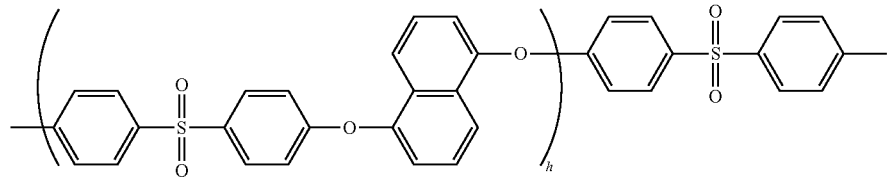
(24j)
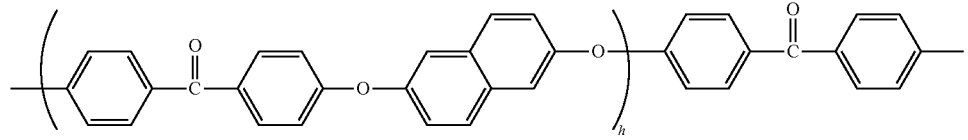
(24k)
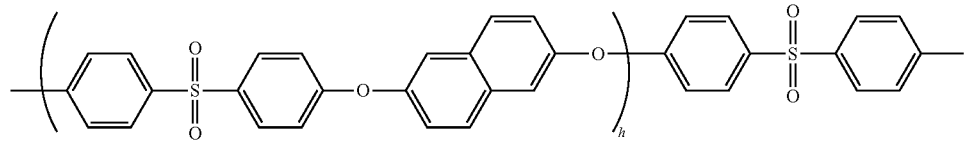
(24l)
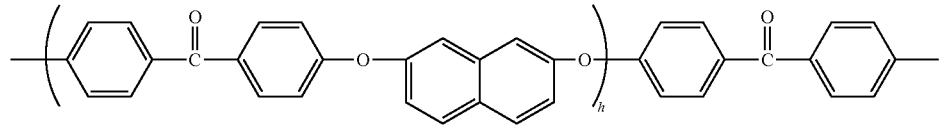
(24m)
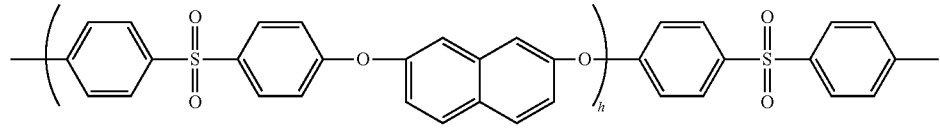
(24n)
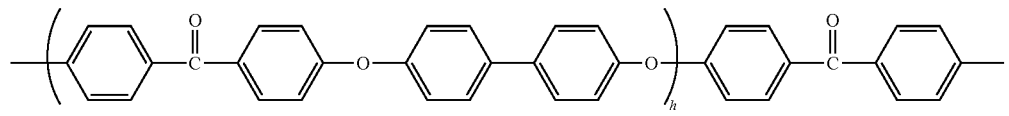
(24o)

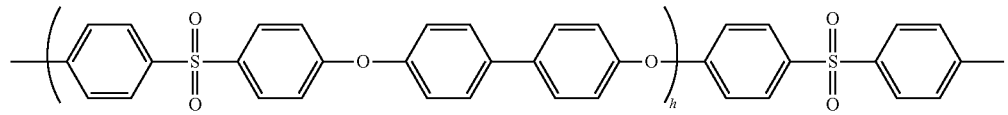 (24p)
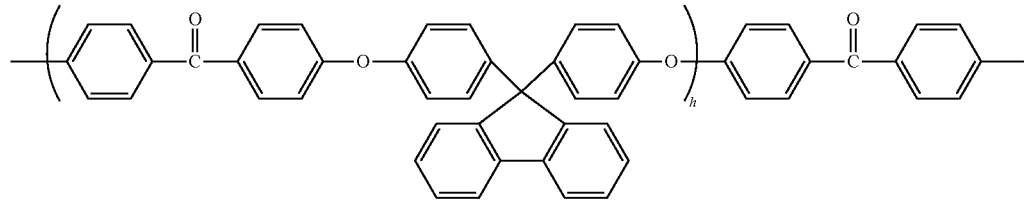 (24q)
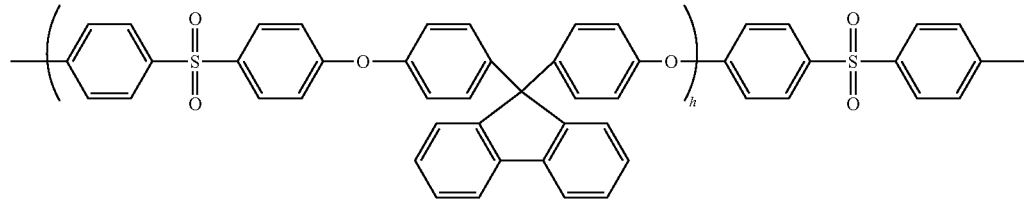 (24r)
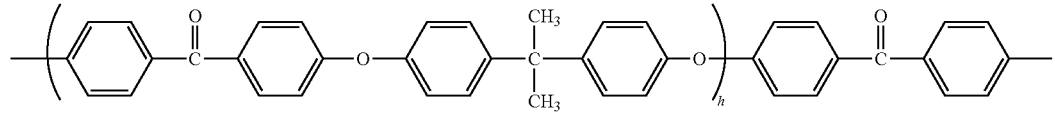 (24s)
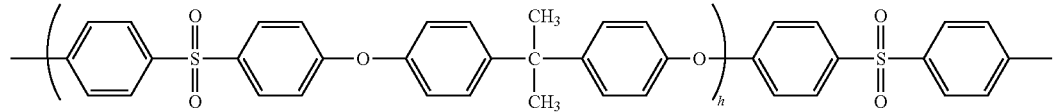 (24t)
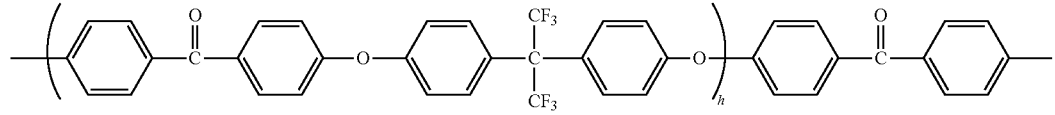 (24u)
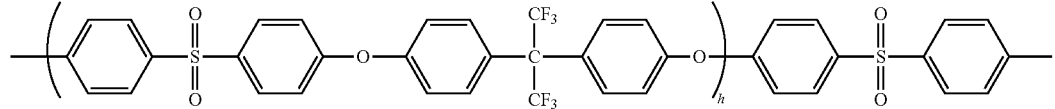 (24v)
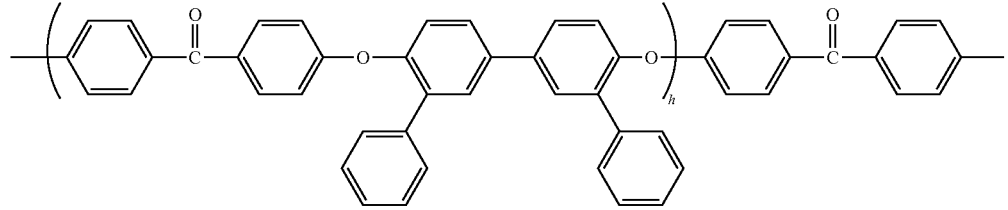 (24w)
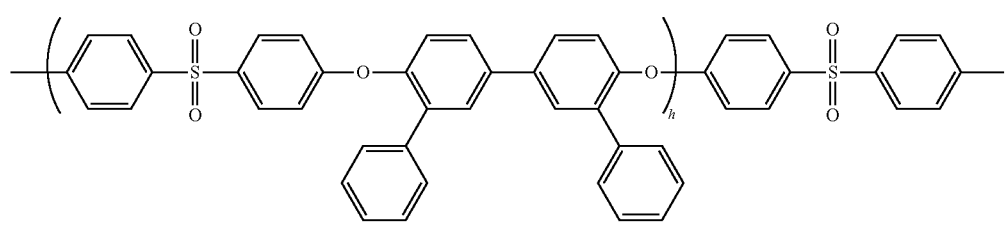 (24x)

Examples of the conjugated aromatic compound comprising the repeating unit derived from the aromatic compound having two leaving groups and the segment represented by the formula (24) include a conjugated aromatic compound comprising any one repeating units of the repeating units represented by the above-mentioned formulae (21a) to (21d) and any one segment of the segments represented by the above-mentioned formulae (24a) to (24x). Specific examples thereof include conjugated aromatic compounds represented by the following formulae (I-1) to (I-16). Herein, in the following formulae, h represents the same meaning as defined above, and p represents an integer of 2 or more.

(I-1)
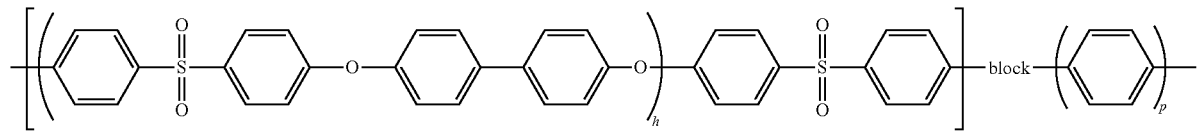

(I-2)
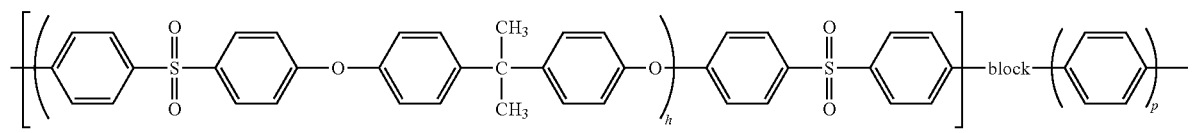

(I-3)
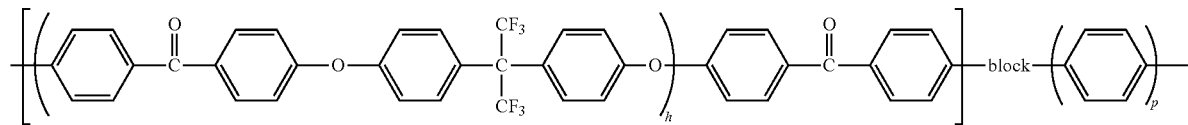

(I-4)
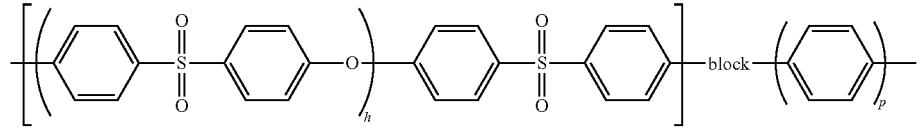

(I-9)
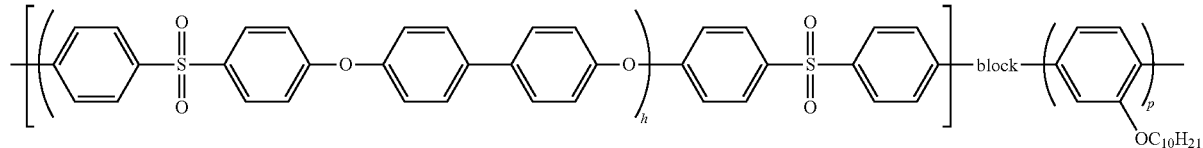

(I-10)
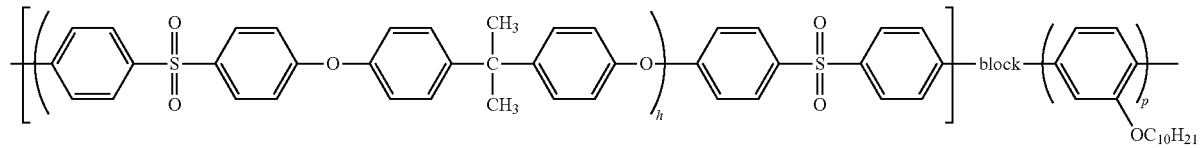

(I-11)
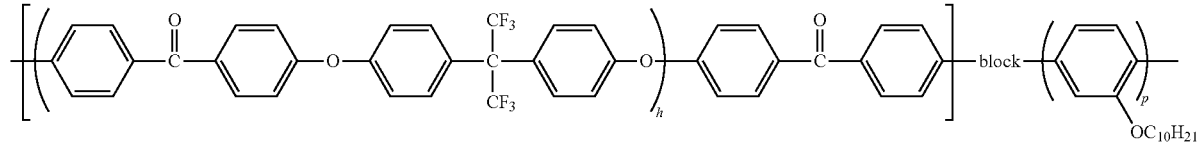

(I-12)
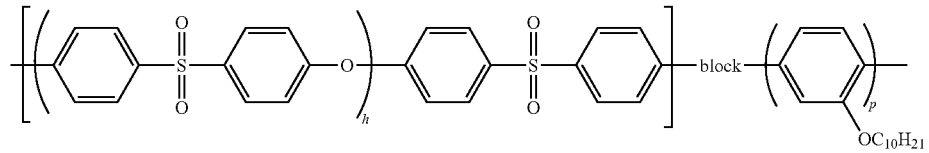

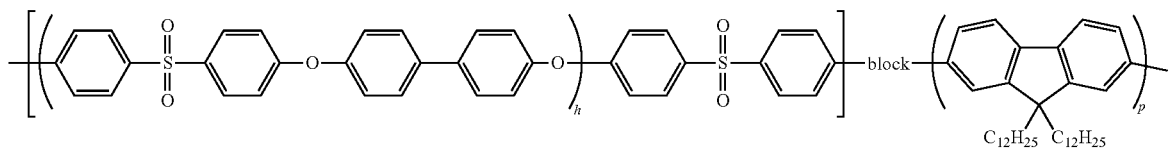
(I-13)

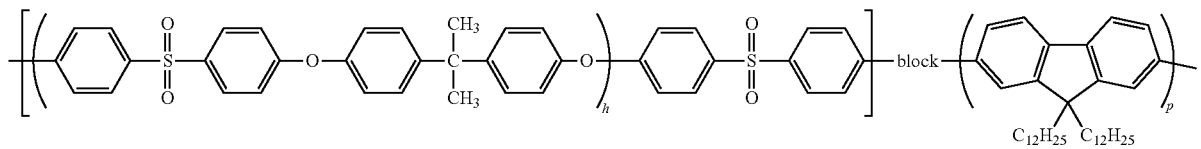
(I-14)

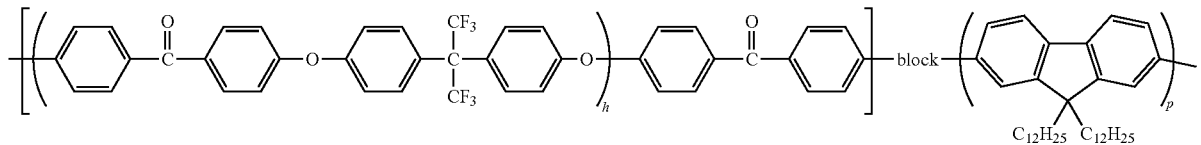
(I-15)

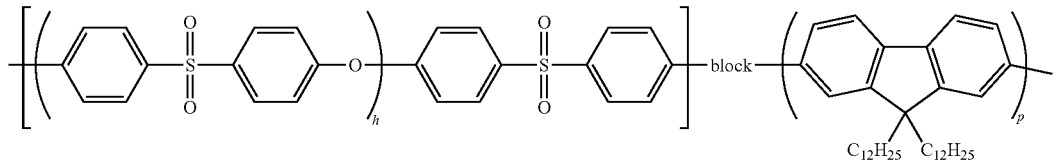
(I-16)

The amount of the segment represented by the formula (24) in the conjugated aromatic compound is preferably 5% by weight or more and 95% by weight or less, and more preferably 10% by weight or more and 70% by weight or less.

When the aromatic compound represented by the formula (5) is used as the aromatic compound (A) and the aromatic compound represented by the formula (6) is used as the aromatic compound (B), examples of the conjugated aromatic compound obtained include a conjugated aromatic compound comprising the repeating unit represented by the above-mentioned formula (23) and the segment represented by the formula (24). Examples of the conjugated aromatic compound comprising the repeating unit represented by the above-mentioned formula (23) and the segment represented by the formula (24) include a conjugated aromatic compound comprising any one repeating unit of the repeating units represented by the above-mentioned formulae (23a) to (23d) and any one segment of the segments represented by the above-mentioned formulae (24a) to (24x). Specific examples thereof include conjugated aromatic compounds represented by the following formulae (III-1) to (III-6). Herein, in the following formulae, h represents the same meanings as defined above and p represents an integer of 2 or more.

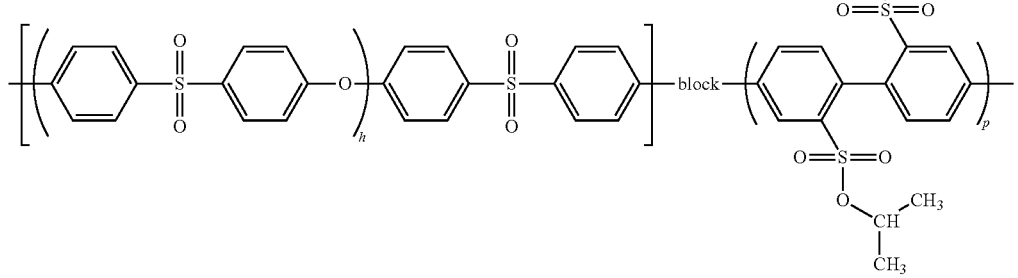
(III-1)

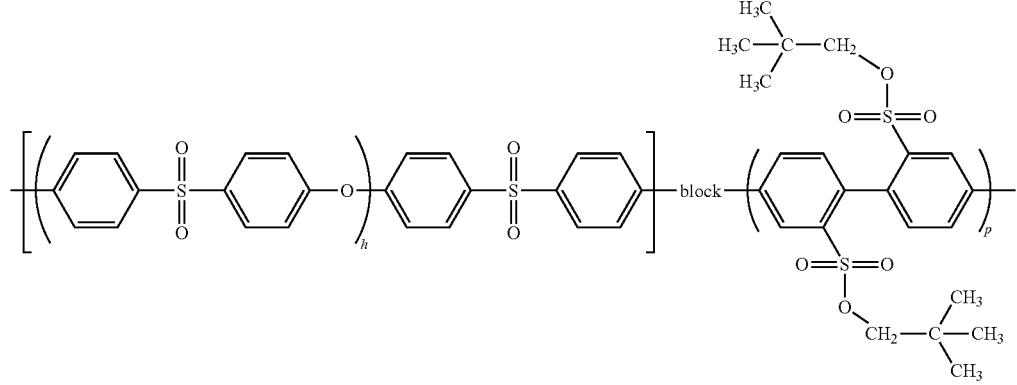
(III-2)
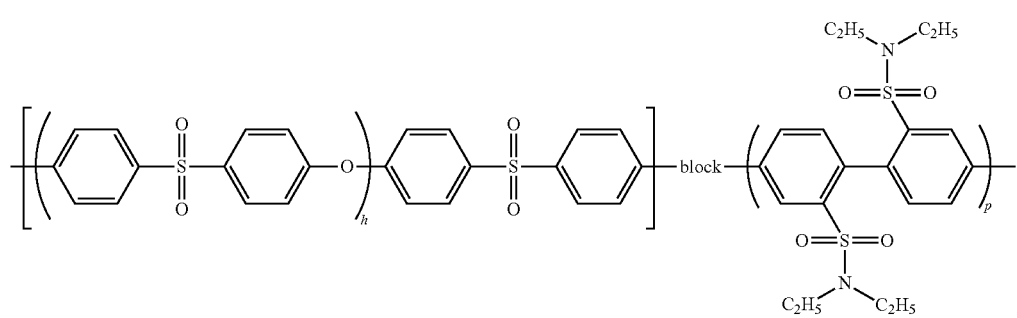
(III-3)
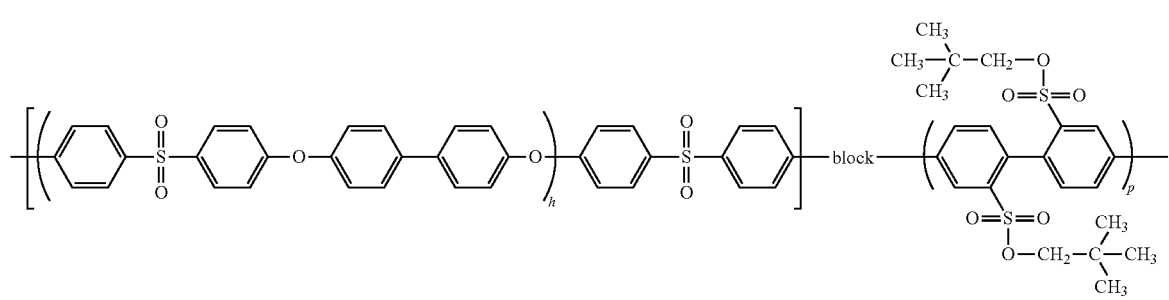
(III-4)
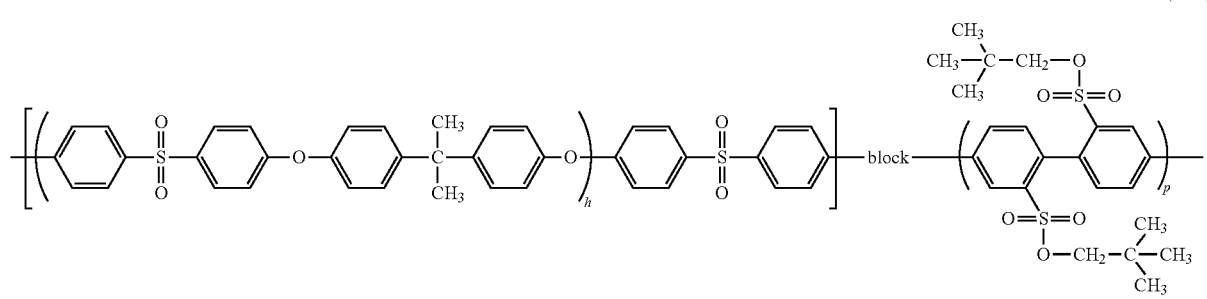
(III-5)

(III-6)

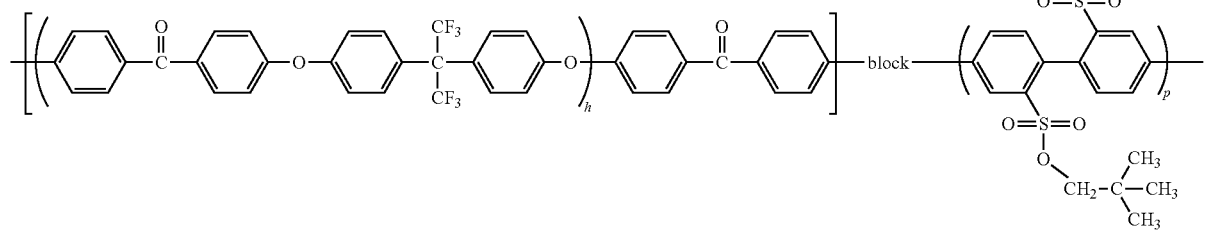

The conjugated aromatic compound usually contains the repeating unit represented by the formula (23) of 2 to 10,000, and the weight-average molecular weight thereof equivalent to polystyrene is usually 1,000 to 6,000,000.

The content of each of repeating units in the conjugated aromatic compound comprising two or more kinds of the repeating units can be adjusted by arbitrarily adjusting the used amount of the aromatic compounds used.

Especially, the conjugated aromatic compound comprising the repeating unit represented by the formula (23) can be used as a law material for synthesizing a polyelectrolyte for a polymer electrolyte fuel cell, and the preferable weight-average molecular weight equivalent to polystyrene in such case is 2,000 to 1,000,000 and more preferable one is 3,000 to 800,000.

EXAMPLES

The present invention will be further illustrated by Examples in more detail below, but the present invention is not limited to these Examples. When the conjugated aromatic compound obtained was not a polymer, it was analyzed with gas chromatography internal standard method or liquid chromatography internal standard method, and the yield thereof was calculated from their results. When the conjugated aromatic compound obtained was a polymer, it was analyzed with gel permeation chromatography (hereinafter, simply referred to as GPC), of which analytical condition was as followed, and the weight-average molecular weight (Mw) and the number-average molecular weight (Mn) thereof equivalent to polystyrene were calculated from its result.
<Analytical Condition>
GPC measuring apparatus: CTO-10A (manufactured by Shimadzu Corporation)
Column: TSK-GEL (manufactured by Tosoh Coporation)
Column temperature: 40° C.
Eluent: N,N-dimethylacetamide containing lithium bromide (concentration of lithium bromide: 10 mmol/dm$^3$)
Flow rate: 0.5 mL/minute
Detection wavelength: 300 nm
However, in Examples 30 to 35 and Comparative Examples 36 to 41, the analysis was conducted using tetrahydrofuran as eluent and at the flow rate of 1.0 mL/minute.

Example 1

To a reaction container made of glass and equipped with a cooling apparatus, 3.1 mg of nickel bromide, 1.9 mg of 4,4'-bis(1,1-dimethylethyl)-2,2'-bipyridine, 1.9 mg of 4,4'-bis(methoxycarbonyl)-2,2'-bipyridine and 93.4 mg of zinc powder were added in an atmosphere of nitrogen at room temperature. To the mixture obtained, 184 mg of 2,2-dimethylpropyl 3-chlorobenzenesulfonate and 5 mL of N,N-dimethylacetamide were added at room temperature. The reaction was conducted by stirring the mixture obtained at 70° C. for 4 hours to obtain a reaction mixture containing 2,2-dimethylpropyl biphenyl-2,2'-disulfonate. The yield of 2,2-dimethylpropyl biphenyl-2,2'-disulfonate was 157 mg.

Example 2

The reaction was conducted according to the same manner as that of Example 1, except that 1.5 mg of 4,4'-dimethoxy-2,2'-bipyridine was used in place of 1.9 mg of 4,4'-bis(1,1-dimethylethyl)-2,2'-bipyridine, a reaction mixture containing 2,2-dimethylpropyl biphenyl-2,2'-disulfonate was obtained. The yield of 2,2-dimethylpropyl biphenyl-2,2'-disulfonate was 154 mg.

Example 3

The reaction was conducted according to the same manner as that of Example 1, except that 1.3 mg of 4,4'-dimethyl-2,2'-bipyridine was used in place of 1.9 mg of 4,4'-bis(1,1-dimethylethyl)-2,2'-bipyridine, a reaction mixture containing 2,2-dimethylpropyl biphenyl-2,2'-disulfonate was obtained. The yield of 2,2-dimethylpropyl biphenyl-2,2'-disulfonate was 159 mg.

Example 4

The reaction was conducted according to the same manner as that of Example 1, except that 2.0 mg of 4,4'-bis(trifluoromethyl)-2,2'-bipyridine was used in place of 1.9 mg of 4,4'-bis(methoxylcarbonyl)-2,2'-bipyridine, a reaction mixture containing 2,2-dimethylpropyl biphenyl-2,2'-disulfonate was obtained. The yield of 2,2-dimethylpropyl biphenyl-2,2'-disulfonate was 153 mg.

Example 5

The reaction was conducted according to the same manner as that of Example 1, except that 1.5 mg of 4,4'-dimethoxy-2,2'-bipyridine was used in place of 1.9 mg of 4,4'-bis(1,1-dimethylethyl)-2,2'-bipyridine and 2.0 mg of 4,4'-bis(trifluoromethyl)-2,2'-bipyridine was used in place of 1.9 mg of 4,4'-bis(methoxylcarbonyl)-2,2'-bipyridine, a reaction mixture containing 2,2-dimethylpropyl biphenyl-2,2'-disulfonate was obtained. The yield of 2,2-dimethylpropyl biphenyl-2,2'-disulfonate was 127 mg.

Comparative Example 1

The reaction was conducted according to the same manner as that of Example 1, except that 2.2 mg of 2,2'-bipyridine was used in place of 1.9 mg of 4,4'-bis(1,1-dimethylethyl)-2,2'-bipyridine and 1.9 mg of 4,4'-bis(methoxylcarbonyl)-2,2'-bipyridine, a reaction mixture containing 2,2-dimethylpropyl biphenyl-2,2'-disulfonate was obtained. The yield of 2,2-dimethylpropyl biphenyl-2,2'-disulfonate was 12 mg.

Comparative Example 2

The reaction was conducted according to the same manner as that of Example 1, except that 3.0 mg of 4,4'-dimethoxy-2,2'-bipyridine was used in place of 1.9 mg of 4,4'-bis(1,1-dimethylethyl)-2,2'-bipyridine and 1.9 mg of 4,4'-bis(methoxylcarbonyl)-2,2'-bipyridine, a reaction mixture containing 2,2-dimethylpropyl biphenyl-2,2'-disulfonate was obtained. The yield of 2,2-dimethylpropyl biphenyl-2,2'-disulfonate was 3 mg.

Comparative Example 3

The reaction was conducted according to the same manner as that of Example 1, except that 3.8 mg of 4,4'-bis(methoxycarbonyl)-2,2'-bipyridine was used in place of 1.9 mg of 4,4'-bis(1,1-dimethylethyl)-2,2'-bipyridine and 1.9 mg of 4,4'-bis(methoxylcarbonyl)-2,2'-bipyridine, a reaction mixture containing 2,2-dimethylpropyl biphenyl-2,2'-disulfonate was obtained. The yield of 2,2-dimethylpropyl biphenyl-2,2'-disulfonate was 5 mg.

Comparative Example 4

The reaction was conducted according to the same manner as that of Example 1, except that 2.6 mg of 4,4'-dimethyl-2,2'-bipyridine was used in place of 1.9 mg of 4,4'-bis(1,1-dimethylethyl)-2,2'-bipyridine and 1.9 mg of 4,4'-bis(methoxylcarbonyl)-2,2'-bipyridine, a reactionmixture containing 2,2-dimethylpropyl biphenyl-2,2'-disulfonate was obtained. The yield of 2,2-dimethylpropyl biphenyl-2,2'-disulfonate was 10 mg.

Comparative Example 5

The reaction was conducted according to the same manner as that of Example 1, except that 3.8 mg of 4,4'-bis(methoxycarbonyl)-2,2'-bipyridine was used in place of 1.9 mg of 4,4'-bis(1,1-dimethylethyl)-2,2'-bipyridine and 1.9 mg of 4,4'-bis(methoxylcarbonyl)-2,2'-bipyridine, a reaction mixture containing 2,2-dimethylpropyl biphenyl-2,2'-disulfonate was obtained. The yield of 2,2-dimethylpropyl biphenyl-2,2'-disulfonate was 4 mg.

Comparative Example 6

The reaction was conducted according to the same manner as that of Example 1, except that 4.1 mg of 4,4'-ditrifluoromethyl-2,2'-bipyridine was used in place of 1.9 mg of 4,4'-bis(1,1-dimethylethyl)-2,2'-bipyridine and 1.9 mg of 4,4'-bis(methoxylcarbonyl)-2,2'-bipyridine, a reaction mixture containing 2,2-dimethylpropyl biphenyl-2,2'-disulfonate was obtained. The yield of 2,2-dimethylpropyl biphenyl-2,2'-disulfonate was 70 mg.

Example 6

To a reaction container made of glass and equipped with a cooling apparatus, 4.6 mg of nickel bromide, 2.8 mg of 4,4'-bis(1,1-dimethylethyl)-2,2'-bipyridine, 2.9 mg of 4,4'-bis(methoxycarbonyl)-2,2'-bipyridine and 94.3 mg of zinc powder were added in an atmosphere of nitrogen at room temperature. To the mixture obtained, 108 mg of 4-chloroacetophenone and 5 mL of N,N-dimethylacetamide were added at room temperature. The reaction was conducted by stirring the mixture obtained at 70° C. for 4 hours to obtain a reaction mixture containing 4,4'-diacetylbiphenyl. The yield of 4,4'-diacetylbiphenyl was 77 mg.

Example 7

The reaction was conducted according to the same manner as that of Example 6, except that 1.9 mg of 4,4'-dimethyl-2,2'-bipyridine was used in place of 2.8 mg of 4,4'-bis(1,1-dimethylethyl)-2,2'-bipyridine and 3.1 mg of 4,4'-bis(trifluoromethyl)-2,2'-bipyridine was used in place of 2.9 mg of 4,4'-bis(methoxycarbonyl)-2,2'-bipyridine, a reaction mixture containing 4,4'-diacetylbiphenyl was obtained. The yield of 4,4'-diacetylbiphenyl was 78 mg.

Comparative Example 7

The reaction was conducted according to the same manner as that of Example 6, except that 3.3 mg of 2,2'-bipyridine was used in place of 2.8 mg of 4,4'-bis(1,1-dimethylethyl)-2,2'-bipyridine and 2.9 mg of 4,4'-bis(methoxycarbonyl)-2,2'-bipyridine, a reaction mixture containing 4,4'-diacetylbiphenyl was obtained. The yield of 4,4'-diacetylbiphenyl was 52 mg.

Comparative Example 8

The reaction was conducted according to the same manner as that of Example 6, except that 5.6 mg of 4,4'-bis(1,1-dimethylethyl)-2,2'-bipyridine was used in place of 2.8 mg of 4,4'-bis(1,1-dimethylethyl)-2,2'-bipyridine and 2.9 mg of 4,4'-bis(methoxycarbonyl)-2,2'-bipyridine, a reaction mixture containing 4,4'-diacetylbiphenyl was obtained. The yield of 4,4'-diacetylbiphenyl was 4 mg.

Comparative Example 9

The reaction was conducted according to the same manner as that of Example 6, except that 3.9 mg of 4,4'-dimethyl-2,2'-bipyridine was used in place of 2.8 mg of 4,4'-bis(1,1-dimethylethyl)-2,2'-bipyridine and 2.9 mg of 4,4'-bis(methoxycarbonyl)-2,2'-bipyridine, a reaction mixture containing 4,4'-diacetylbiphenyl was obtained. The yield of 4,4'-diacetylbiphenyl was 9 mg.

Comparative Example 10

The reaction was conducted according to the same manner as that of Example 6, except that 5.7 mg of 4,4'-bis(methoxycarbonyl)-2,2'-bipyridine was used in place of 2.8 mg of 4,4'-bis(1,1-dimethylethyl)-2,2'-bipyridine and 2.9 mg of 4,4'-bis(methoxycarbonyl)-2,2'-bipyridine, a reaction mixture containing 4,4'-diacetylbiphenyl was obtained. The yield of 4,4'-diacetylbiphenyl was 18 mg.

Comparative Example 11

The reaction was conducted according to the same manner as that of Example 6, except that 6.1 mg of 4,4-bis(trifluoromethyl)-2,2'-bipyridine was used in place of 2.8 mg of 4,4'-bis(1,1-dimethylethyl)-2,2'-bipyridine and 2.9 mg of 4,4'-bis(methoxycarbonyl)-2,2'-bipyridine, a reaction mixture containing 4,4'-diacetylbiphenyl was obtained. The yield of 4,4'-diacetylbiphenyl was 54 mg.

Example 8

To a reaction container made of glass and equipped with a cooling apparatus, 4.6 mg of nickel bromide, 2.8 mg of 4,4'-bis(1,1-dimethylethyl)-2,2'-bipyridine, 2.9 mg of 4,4'-bis(methoxycarbonyl)-2,2'-bipyridine and 94.3 mg of zinc powder were added in an atmosphere of nitrogen at room temperature. To the mixture obtained, 96 mg of 4-chlorobenzonitrile and 5 mL of N,N-dimethylacetamide were added at room temperature. The reaction was conducted by stirring the mixture obtained at 70° C. for 4 hours to obtain a reaction mixture containing 4,4'-dicyanobiphenyl. The yield of 4,4'-dicyanobiphenyl was 38 mg.

Example 9

The reaction was conducted according to the same manner as that of Example 8, except that 2.3 mg of 4,4'-dimethoxy-2,2'-bipyridine was used in place of 2.8 mg of 4,4'-bis(1,1-dimethylethyl)-2,2'-bipyridine and 3.1 mg of 4,4'-bis(trifluoromethyl)-2,2'-bipyridine was used in place of 2.9 mg of 4,4'-bis(methoxycarbonyl)-2,2'-bipyridine, a reaction mixture containing 4,4'-dicyanobiphenyl was obtained. The yield of 4,4'-dicyanobiphenyl was 47 mg.

Comparative Example 12

The reaction was conducted according to the same manner as that of Example 8, except that 4.5 mg of 4,4'-dimethoxy-2,2'-bipyridine was used in place of 2.8 mg of 4,4'-bis(1,1-dimethylethyl)-2,2'-bipyridine and 2.9 mg of 4,4'-bis(methoxycarbonyl)-2,2'-bipyridine, a reaction mixture containing 4,4'-dicyanobiphenyl was obtained. The yield of 4,4'-dicyanobiphenyl was 17 mg.

Comparative Example 13

The reaction was conducted according to the same manner as that of Example 8, except that 5.6 mg of 4,4'-bis(1,1-dimethylethyl)-2,2'-bipyridine was used in place of 2.8 mg of 4,4'-bis(1,1-dimethylethyl)-2,2'-bipyridine and 2.9 mg of 4,4'-bis(methoxycarbonyl)-2,2'-bipyridine, a reaction mixture containing 4,4'-dicyanobiphenyl was obtained. The yield of 4,4'-dicyanobiphenyl was 18 mg.

Comparative Example 14

The reaction was conducted according to the same manner as that of Example 8, except that 5.7 mg of 4,4'-bis(methoxycarbonyl)-2,2'-bipyridine was used in place of 2.8 mg of 4,4'-bis(1,1-dimethylethyl)-2,2'-bipyridine and 2.9 mg of 4,4'-bis(methoxycarbonyl)-2,2'-bipyridine, a reaction mixture containing 4,4'-dicyanobiphenyl was obtained. The yield of 4,4'-dicyanobiphenyl was 9 mg.

Comparative Example 15

The reaction was conducted according to the same manner as that of Example 8, except that 6.1 mg of 4,4'-bis(trifluoromethyl)-2,2'-bipyridine was used in place of 2.8 mg of 4,4'-bis(1,1-dimethylethyl)-2,2'-bipyridine and 2.9 mg of 4,4'-bis(methoxycarbonyl)-2,2'-bipyridine, a reaction mixture containing 4,4'-dicyanobiphenyl was obtained. The yield of 4,4'-dicyanobiphenyl was 18 mg.

Example 10

To a reaction container made of glass and equipped with a cooling apparatus, 7.6 mg of nickel bromide, 4.7 mg of 4,4'-bis(1,1-dimethylethyl)-2,2'-bipyridine, 4.7 mg of 4,4'-bis(methoxycarbonyl)-2,2'-bipyridine and 96.1 mg of zinc powder were added in an atmosphere of nitrogen at room temperature. To the mixture obtained, 91 mg of 4-chlorofluorobenzene and 5 mL of N,N-dimethylacetamide were added at room temperature. The reaction was conducted by stirring the mixture obtained at 70° C. for 4 hours to obtain a reaction mixture containing 4,4'-difluorobiphenyl. The yield of 4,4'-difluorobiphenyl was 44 mg.

Comparative Example 16

The reaction was conducted according to the same manner as that of Example 10, except that 5.4 mg of 2,2'-bipyridine was used in place of 4.7 mg of 4,4'-bis(1,1-dimethylethyl)-2,2'-bipyridine and 4.7 mg of 4,4'-bis(methoxycarbonyl)-2,2'-bipyridine, a reaction mixture containing 4,4'-difluorobiphenyl was obtained. The yield of 4,4'-difluorobiphenyl was 38 mg.

Comparative Example 17

The reaction was conducted according to the same manner as that of Example 10, except that 9.4 mg of 4,4'-bis(1,1-dimethylethyl)-2,2'-bipyridine was used in place of 4.7 mg of 4,4'-bis(1,1-dimethylethyl)-2,2'-bipyridine and 4.7 mg of 4,4'-bis(methoxycarbonyl)-2,2'-bipyridine, a reaction mixture containing 4,4'-difluorobiphenyl was obtained. The yield of 4,4'-difluorobiphenyl was 25 mg.

Comparative Example 18

The reaction was conducted according to the same manner as that of Example 10, except that 9.5 mg of 4,4'-bis(methoxycarbonyl)-2,2'-bipyridine was used in place of 4.7 mg of 4,4'-bis(1,1-dimethylethyl)-2,2-bipyridine and 4.7 mg of 4,4'-bis(methoxycarbonyl)-2,2'-bipyridine, a reaction mixture containing 4,4'-difluorobiphenyl was obtained. The yield of 4,4'-difluorobiphenyl was 6 mg.

Example 11

To a reaction container made of glass and equipped with a cooling apparatus, 7.6 mg of nickel bromide, 4.7 mg of 4,4'-bis(1,1-dimethylethyl)-2,2'-bipyridine, 4.7 mg of 4,4'-bis(methoxycarbonyl)-2,2'-bipyridine and 96.1 mg of zinc powder were added in an atmosphere of nitrogen at room temperature. To the mixture obtained, 100 mg of 4-chloroanisole and 5 mL of N,N-dimethylacetamide were added at room temperature. The reaction was conducted by stirring the mixture obtained at 70° C. for 4 hours to obtain a reaction mixture containing 4,4'-dimethoxybiphenyl. The yield of 4,4'-dimethoxybiphenyl was 40 mg.

Comparative Example 19

The reaction was conducted according to the same manner as that of Example 11, except that 5.4 mg of 2,2'-bipyridine was used in place of 4.7 mg of 4,4'-bis(1,1-dimethylethyl)-2,2'-bipyridine and 4.7 mg of 4,4'-bis(methoxycarbonyl)-2,2'-bipyridine, a reaction mixture containing 4,4'-dimethoxybiphenyl was obtained. The yield of 4,4'-dimethoxybiphenyl was 27 mg.

Comparative Example 20

The reaction was conducted according to the same manner as that of Example 11, except that 9.4 mg of 4,4'-bis(1,1-dimethylethyl)-2,2'-bipyridine was used in place of 4.7 mg of 4,4'-bis(1,1-dimethylethyl)-2,2'-bipyridine and 4.7 mg of 4,4'-bis(methoxycarbonyl)-2,2'-bipyridine, a reaction mixture containing 4,4'-dimethoxybiphenyl was obtained. The yield of 4,4'-dimethoxybiphenyl was 38 mg.

Comparative Example 21

The reaction was conducted according to the same manner as that of Example 11, except that 9.5 mg of 4,4'-bis(methoxycarbonyl)-2,2'-bipyridine was used in place of 4.7 mg of 4,4'-bis(1,1-dimethylethyl)-2,2'-bipyridine and 4.7 mg of 4,4'-bis(methoxycarbonyl)-2,2'-bipyridine, a reaction mixture containing 4,4'-dimethoxybiphenyl was obtained. The yield of 4,4'-dimethoxybiphenyl was 3 mg.

Example 12

To a reaction container made of glass and equipped with a cooling apparatus, 7.6 mg of nickel bromide, 4.7 mg of 4,4'-bis(1,1-dimethylethyl)-2,2'-bipyridine, 4.7 mg of 4,4'-bis(methoxycarbonyl)-2,2'-bipyridine and 96.1 mg of zinc powder were added in an atmosphere of nitrogen at room temperature. To the mixture obtained, 100 mg of 3-chloroanisole and 5 mL of N,N-dimethylacetamide were added at room temperature. The reaction was conducted by stirring the mixture obtained at 70° C. for 4 hours to obtain a reaction mixture containing 3,3'-dimethoxybiphenyl. The yield of 3,3'-dimethoxybiphenyl was 54 mg.

Comparative Example 22

The reaction was conducted according to the same manner as that of Example 12, except that 5.4 mg of 2,2'-bipyridine was used in place of 4.7 mg of 4,4'-bis(1,1-dimethylethyl)-2,2'-bipyridine and 4.7 mg of 4,4'-bis(methoxycarbonyl)-2,2'-bipyridine, a reaction mixture containing 3,3'-dimethoxybiphenyl was obtained. The yield of 3,3'-dimethoxybiphenyl was 45 mg.

Comparative Example 23

The reaction was conducted according to the same manner as that of Example 12, except that 9.4 mg of 4,4'-bis(1,1-dimethylethyl)-2,2'-bipyridine was used in place of 4.7 mg of 4,4-bis(1,1-dimethylethyl)-2,2'-bipyridine and 4.7 mg of 4,4'-bis(methoxycarbonyl)-2,2-bipyridine, a reaction mixture containing 3,3'-dimethoxybiphenyl was obtained. The yield of 3,3'-dimethoxybiphenyl was 50 mg.

Comparative Example 24

The reaction was conducted according to the same manner as that of Example 12, except that 9.5 mg of 4,4'-bis(dimethoxycarbonyl)-2,2-bipyridine was used in place of 4.7 mg of 4,4'-bis(1,1-dimethylethyl)-2,2'-bipyridine and 4.7 mg of 4,4'-bis(methoxycarbonyl)-2,2'-bipyridine, a reaction mixture containing 3,3'-dimethoxybiphenyl was obtained. The yield of 3,3'-dimethoxybiphenyl was 4 mg.

Example 13

To a reaction container made of glass and equipped with a cooling apparatus, 7.6 mg of nickel bromide, 4.7 mg of 4,4'-bis(1,1-dimethylethyl)-2,2'-bipyridine, 4.7 mg of 4,4'-bis(methoxycarbonyl)-2,2'-bipyridine and 96.1 mg of zinc powder were added in an atmosphere of nitrogen at room temperature. To the mixture obtained, 100 mg of 2-chloroanisole and 5 mL of N,N-dimethylacetamide were added at room temperature. The reaction was conducted by stirring the mixture obtained at 70° C. for 4 hours to obtain a reaction mixture containing 2,2'-dimethoxybiphenyl. The yield of 2,2'-dimethoxybiphenyl was 26 mg.

Comparative Example 25

The reaction was conducted according to the same manner as that of Example 13, except that 5.4 mg of 2,2'-bipyridine was used in place of 4.7 mg of 4,4-bis(1,1-dimethylethyl)-2,2'-bipyridine and 4.7 mg of 4,4'-bis(methoxycarbonyl)-2,2'-bipyridine, a reaction mixture containing 2,2'-dimethoxybiphenyl was obtained. The yield of 2,2'-dimethoxybiphenyl was 19 mg.

Comparative Example 26

The reaction was conducted according to the same manner as that of Example 13, except that 9.4 mg of 4,4'-bis(1,1-dimethylethyl)-2,2'-bipyridine was used in place of 4.7 mg of 4,4'-bis(1,1-dimethylethyl)-2,2'-bipyridine and 4.7 mg of 4,4'-bis(methoxycarbonyl)-2,2-bipyridine, a reaction mixture containing 2,2'-dimethoxybiphenyl was obtained. The yield of 2,2'-dimethoxybiphenyl was 13 mg.

Comparative Example 27

The reaction was conducted according to the same manner as that of Example 13, except that 9.5 mg of 4,4'-bis(dimethoxycarbonyl)-2,2'-bipyridine was used in place of 4.7 mg of 4,4'-bis(1,1-dimethylethyl)-2,2'-bipyridine and 4.7 mg of 4,4'-bis(methoxycarbonyl)-2,2'-bipyridine. However, the production of 2,2'-dimethoxybiphenyl was not found.

Example 14

To a reaction container made of glass and equipped with a cooling apparatus, 7.6 mg of nickel bromide, 4.7 mg of 4,4'-bis(1,1-dimethylethyl)-2,2'-bipyridine, 4.7 mg of 4,4'-bis(methoxycarbonyl)-2,2'-bipyridine, 96.1 mg of zinc powder, 2 mL of N,N-dimethylacetamide and a solution obtained by dissolving 366 mg of di(2,2-dimethylpropyl) 4,4'-dichlorobiphenyl-2,2'-disulfonate in 3 mL of N,N-dimethylacetamide were added in an atmosphere of nitrogen at room temperature. The reaction was conducted by stirring the mixture obtained at 70° C. for 4 hours to obtain a reaction mixture containing a conjugated aromatic compound consisting of a repeating unit represented by the following formula (i). Mw of the conjugated aromatic compound was 716,000, and Mn thereof was 189,000.

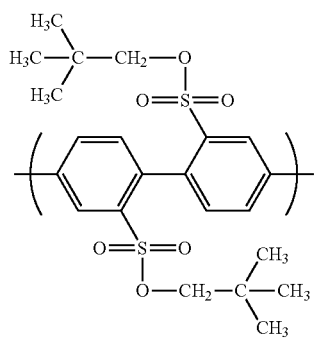

(i)

Example 15

The reaction was conducted according to the same manner as that of Example 14, except that 5.1 mg of 4,4'-bis(trifluoromethyl)-2,2'-bipyridine was used in place of 4.7 mg of 4,4'-bis(methoxycarbonyl)-2,2'-bipyridine, a reaction mixture containing a conjugated aromatic compound consisting of a repeating unit represented by the above-mentioned formula (i) was obtained. Mw of the conjugated aromatic compound was 517,000, and Mn thereof was 136,000.

Example 16

The reaction was conducted according to the same manner as that of Example 14, except that 4.7 mg of 5,5'-bis(methoxycarbonyl)-2,2'-bipyridine was used in place of 4.7 mg of 4,4'-bis(methoxycarbonyl)-2,2'-bipyridine, a reaction mixture containing a conjugated aromatic compound consisting of a repeating unit represented by the above-mentioned formula (i) was obtained. Mw of the conjugated aromatic compound was 552,000, and Mn thereof was 159,000.

Example 17

The reaction was conducted according to the same manner as that of Example 14, except that 3.2 mg of 4,4'-dimethyl-2, 2'-bipyridine was used in place of 4.7 mg of 4,4'-bis(1,1-dimethylethyl)-2,2'-bipyridine, a reaction mixture containing a conjugated aromatic compound consisting of a repeating unit represented by the above-mentioned formula (i) was obtained. Mw of the conjugated aromatic compound was 197,000, and Mn thereof was 61,000.

Example 18

The reaction was conducted according to the same manner as that of Example 14, except that 3.2 mg of 5,5'-dimethyl-2, 2'-bipyridine was used in place of 4.7 mg of 4,4'-bis(1,1-dimethylethyl)-2,2'-bipyridine, a reaction mixture containing a conjugated aromatic compound consisting of a repeating unit represented by the above-mentioned formula (i) was obtained. Mw of the conjugated aromatic compound was 227,000, and Mn thereof was 67,000.

Example 19

The reaction was conducted according to the same manner as that of Example 14, except that 3.2 mg of 4,4'-dimethyl-2, 2'-bipyridine was used in place of 4.7 mg of 4,4'-bis(1,1-dimethylethyl)-2,2'-bipyridine and 5.1 mg of 4,4'-bis(trifluoromethyl)-2,2'-bipyridine was used in place of 4.7 mg of 4,4'-bis(methoxycarbonyl)-2,2'-bipyridine, a reaction mixture containing a conjugated aromatic compound consisting of a repeating unit represented by the above-mentioned formula (i) was obtained. Mw of the conjugated aromatic compound was 126,000, and Mn thereof was 41,000.

Example 20

The reaction was conducted according to the same manner as that of Example 14, except that 3.2 mg of 4,4'-dimethyl-2, 2'-bipyridine was used in place of 4.7 mg of 4,4'-bis(1,1-dimethylethyl)-2,2'-bipyridine and 4.7 mg of 5,5'-bis(methoxycarbonyl)-2,2'-bipyridine was used in place of 4.7 mg of 4,4-bis(methoxycarbonyl)-2,2'-bipyridine, a reaction mixture containing a conjugated aromatic compound consisting of a repeating unit represented by the above-mentioned formula (i) was obtained. Mw of the conjugated aromatic compound was 82,000, and Mn thereof was 30,000.

Example 21

The reaction was conducted according to the same manner as that of Example 14, except that 3.8 mg of 4,4'-dimethoxy-2,2'-bipyridine was used in place of 4.7 mg of 4,4'-bis(1,1-dimethylethyl)-2,2'-bipyridine, a reaction mixture containing a conjugated aromatic compound consisting of a repeating unit represented by the above-mentioned formula (i) was obtained. Mw of the conjugated aromatic compound was 377,000, and Mn thereof was 112,000.

Example 22

The reaction was conducted according to the same manner as that of Example 14, except that 3.8 mg of 4,4'-dimethoxy-2,2'-bipyridine was used in place of 4.7 mg of 4,4'-bis(1,1-dimethylethyl)-2,2-bipyridine and 5.1 mg of 4,4'-bis(trifluoromethyl)-2,2'-bipyridine was used in place of 4.7 mg of 4,4'-bis(methoxycarbonyl)-2,2'-bipyridine, a reaction mixture containing a conjugated aromatic compound consisting of a repeating unit represented by the above-mentioned formula (i) was obtained. Mw of the conjugated aromatic compound was 84,000, and Mn thereof was 30,000.

Example 23

The reaction was conducted according to the same manner as that of Example 14, except that 3.8 mg of 4,4'-dimethoxy-2,2'-bipyridine was used in place of 4.7 mg of 4,4'-bis(1,1-dimethylethyl)-2,2'-bipyridine and 4.7 mg of 5,5'-bis(methoxycarbonyl)-2,2-bipyridine was used in place of 4.7 mg of 4,4'-bis(methoxycarbonyl)-2,2'-bipyridine, a reaction mixture containing a conjugated aromatic compound consisting of a repeating unit represented by the above-mentioned formula (i) was obtained. Mw of the conjugated aromatic compound was 55,000, and Mn thereof was 23,000.

Comparative Example 28

The reaction was conducted according to the same manner as that of Example 14, except that 6.4 mg of 4,4'-dimethyl-2, 2'-bipyridine was used in place of 4.7 mg of 4,4'-bis(1,1-dimethylethyl)-2,2'-bipyridine and 4.7 mg of 4,4'-bis(methoxycarbonyl)-2,2'-bipyridine, a reaction mixture containing a conjugated aromatic compound consisting of a repeating unit represented by the above-mentioned formula (i) was obtained. Mw of the conjugated aromatic compound was 2,000, and Mn thereof was 2,000.

Comparative Example 29

The reaction was conducted according to the same manner as that of Example 14, except that 9.4 mg of 4,4'-bis(1,1-dimethylethyl)-2,2'-bipyridine was used in place of 4.7 mg of 4,4'-bis(1,1-dimethylethyl)-2,2'-bipyridine and 4.7 mg of 4,4'-bis(methoxycarbonyl)-2,2'-bipyridine, a reaction mixture containing a conjugated aromatic compound consisting of a repeating unit represented by the above-mentioned formula (i) was obtained. Mw of the conjugated aromatic compound was 2,000, and Mn thereof was 2,000.

Comparative Example 30

The reaction was conducted according to the same manner as that of Example 14, except that 7.6 mg of 4,4'-dimethoxy-2,2'-bipyridine was used in place of 4.7 mg of 4,4'-bis(1,1-dimethylethyl)-2,2'-bipyridine and 4.7 mg of 4,4'-bis(methoxycarbonyl)-2,2'-bipyridine, a reaction mixture containing a conjugated aromatic compound consisting of a repeating unit represented by the above-mentioned formula (i) was obtained. Mw of the conjugated aromatic compound was 3,000, and Mn thereof was 2,000.

Comparative Example 31

The reaction was conducted according to the same manner as that of Example 14, except that 9.5 mg of 4,4'-bis(methoxycarbonyl)-2,2'-bipyridine was used in place of 4.7 mg of 4,4'-bis(1,1-dimethylethyl)-2,2'-bipyridine and 4.7 mg of 4,4-bis(methoxycarbonyl)-2,2'-bipyridine, a reaction mixture containing a conjugated aromatic compound consisting of a repeating unit represented by the above-mentioned formula (i) was obtained. Mw of the conjugated aromatic compound was 3,000, and Mn thereof was 3,000.

Comparative Example 32

The reaction was conducted according to the same manner as that of Example 14, except that 9.5 mg of 5,5'-bis(methoxycarbonyl)-2,2'-bipyridine was used in place of 4.7 mg of 4,4'-bis(1,1-dimethylethyl)-2,2'-bipyridine and 4.7 mg of 4,4'-bis(methoxycarbonyl)-2,2-bipyridine, a reaction mixture containing a conjugated aromatic compound consisting of a repeating unit represented by the above-mentioned formula (i) was obtained. Mw of the conjugated aromatic compound was 4,000, and Mn thereof was 3,000.

Comparative Example 33

The reaction was conducted according to the same manner as that of Example 14, except that 10.2 mg of 4,4'-bis(trifluoromethyl)-2,2'-bipyridine was used in place of 4.7 mg of 4,4'-bis(1,1-dimethylethyl)-2,2'-bipyridine and 4.7 mg of 4,4'-bis(methoxycarbonyl)-2,2'-bipyridine, a reaction mixture containing a conjugated aromatic compound consisting of a repeating unit represented by the above-mentioned formula (i) was obtained. Mw of the conjugated aromatic compound was 6,000, and Mn thereof was 4,000.

Example 24

To a reaction container made of glass and equipped with a cooling apparatus, 9.6 mg of bis(cyclooctadiene)nickel(0), 3.2 mg of 5,5'-dimethyl-2,2'-bipyridine, 4.7 mg of 4,4'-bis(methoxycarbonyl)-2,2'-bipyridine, 91.6 mg of zinc powder, 2 mL of N,N-dimethylacetamide and a solution obtained by dissolving 366 mg of di(2,2-dimethylpropyl) 4,4'-dichlorobiphenyl-2,2'-disulfonate in 3 mL of N,N-dimethylacetamide were added in an atmosphere of nitrogen at room temperature. The reaction was conducted by stirring the mixture obtained at 70° C. for 4 hours to obtain a reaction mixture containing a conjugated aromatic compound consisting of the repeating unit represented by the above-mentioned formula (i). Mw of the conjugated aromatic compound was 69,000, and Mn thereof was 27,000.

Comparative Example 34

The reaction was conducted according to the same manner as that of Example 24, except that 6.4 mg of 5,5'-dimethyl-2,2'-bipyridine was used in place of 3.2 mg of 5,5'-dimethyl-2,2'-bipyridine and 4.7 mg of 4,4'-bis(methoxycarbonyl)-2,2'-bipyridine, a reaction mixture containing a conjugated aromatic compound consisting of a repeating unit represented by the above-mentioned formula (i) was obtained. Mw of the conjugated aromatic compound was 4,000, and Mn thereof was 3,000.

Comparative Example 35

The reaction was conducted according to the same manner as that of Example 24, except that 9.5 mg of 4,4'-bis(methoxycarbonyl)-2,2'-bipyridine was used in place of 3.2 mg of 5,5'-dimethyl-2,2'-bipyridine and 4.7 mg of 4,4'-bis(methoxycarbonyl)-2,2'-bipyridine, a reaction mixture containing a conjugated aromatic compound consisting of a repeating unit represented by the above-mentioned formula (i) was obtained. Mw of the conjugated aromatic compound was 3,000, and Mn thereof was 3,000.

Example 25

To a reaction container made of glass and equipped with a cooling apparatus, 4.6 mg of nickel bromide, 5.1 mg of 4,4'-bis(1,1-dimethylethyl)-2,2'-bipyridine, 0.6 mg of 4,4'-bis(methoxycarbonyl)-2,2'-bipyridine, 94.3 mg of zinc powder, 2 mL of N,N-dimethylacetamide and a solution obtained by dissolving 366 mg of di(2,2-dimethylpropyl) 4,4'-dichlorobiphenyl-2,2'-disulfonate in 3 mL of N,N-dimethylacetamide were added in an atmosphere of nitrogen at room temperature. The reaction was conducted by stirring the mixture obtained at 70° C. for 4 hours to obtain a reaction mixture containing a conjugated aromatic compound consisting of the repeating unit represented by the above-mentioned formula (i). Mw of the conjugated aromatic compound was 293,000, and Mn thereof was 81,000.

Example 26

The reaction was conducted according to the same manner as that of Example 25, except that the used amount of 4,4'-bis(1,1-dimethylethyl)-2,2'-bipyridine was changed to 3.9 mg, and the used amount of 4,4'-bis(methoxycarbonyl)-2,2'- bipyridine was changed to 1.7 mg, a reaction mixture containing a conjugated aromatic compound consisting of a repeating unit represented by the above-mentioned formula (i) was obtained. Mw of the conjugated aromatic compound was 203,000, and Mn thereof was 59,000.

Example 27

The reaction was conducted according to the same manner as that of Example 25, except that the used amount of 4,4'-bis(1,1-dimethylethyl)-2,2'-bipyridine was changed to 2.8 mg, and the used amount of 4,4'-bis(methoxycarbonyl)-2,2'-bipyridine was changed to 2.9 mg, a reaction mixture containing a conjugated aromatic compound consisting of a repeating unit represented by the above-mentioned formula (i) was obtained. Mw of the conjugated aromatic compound was 83,000, and Mn thereof was 29,000.

Example 28

The reaction was conducted according to the same manner as that of Example 25, except that the used amount of 4,4'-bis(1,1-dimethylethyl)-2,2'-bipyridine was changed to 1.7 mg, and the used amount of 4,4'-bis(methoxycarbonyl)-2,2'-bipyridine was changed to 4.0 mg, a reaction mixture containing a conjugated aromatic compound consisting of a repeating unit represented by the above-mentioned formula (i) was obtained. Mw of the conjugated aromatic compound was 23,000, and Mn thereof was 11,000.

Example 29

The reaction was conducted according to the same manner as that of Example 25, except that the used amount of 4,4'-bis(1,1-dimethylethyl)-2,2'-bipyridine was changed to 0.6 mg, and the used amount of 4,4'-bis(methoxycarbonyl)-2,2'-bipyridine was changed to 5.1 mg, a reaction mixture containing a conjugated aromatic compound consisting of a repeating unit represented by the above-mentioned formula (i) was obtained. Mw of the conjugated aromatic compound was 5,000, and Mn thereof was 4,000.

Example 30

To a reaction container made of glass and equipped with a cooling apparatus, 30.6 mg of nickel bromide, 12.9 mg of 5,5'-dimethyl-2,2'-bipyridine, 19.1 mg of 4,4'-bis(methoxycarbonyl)-2,2'-bipyridine, 109.9 mg of zinc powder, 2 mL of N,N-dimethylacetamide and a solution obtained by dissolving 462 mg of 2,7-dibromo-9,9-didodecyl-9H-fluorene in 3 mL of N,N-dimethylacetamide were added in an atmosphere of nitrogen at room temperature. The reaction was conducted by stirring the mixture obtained at 70° C. for 4 hours to obtain a reaction mixture containing a conjugated aromatic compound consisting of the repeating unit represented by the following formula (ii). Mw of the conjugated aromatic compound was 78,000, and Mn thereof was 21,000.

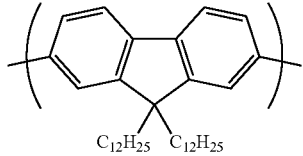

(ii)

Example 31

The reaction was conducted according to the same manner as that of Example 30, except that 12.9 mg of 4,4'-dimethyl-2,2'-bipyridine was used in place of 12.9 mg of 5,5'-dimethyl-2,2'-bipyridine, a reaction mixture containing a conjugated aromatic compound consisting of a repeating unit represented by the above-mentioned formula (ii) was obtained. Mw of the conjugated aromatic compound was 72,000, and Mn thereof was 18,000.

Example 32

The reaction was conducted according to the same manner as that of Example 30, except that 15.1 mg of 4,4'-dimethoxy-2,2'-bipyridine was used in place of 12.9 mg of 5,5'-dimethyl-2,2'-bipyridine, a reaction mixture containing a conjugated aromatic compound consisting of a repeating unit represented by the above-mentioned formula (ii) was obtained. Mw of the conjugated aromatic compound was 63,000, and Mn thereof was 13,000.

Example 33

The reaction was conducted according to the same manner as that of Example 30, except that 18.8 mg of 4,4'-bis(1,1-dimethylethyl)-2,2'-bipyridine was used in place of 12.9 mg of 5,5'-dimethyl-2,2'-bipyridine, a reaction mixture containing a conjugated aromatic compound consisting of a repeating unit represented by the above-mentioned formula (ii) was obtained. Mw of the conjugated aromatic compound was 79,000, and Mn thereof was 25,000.

Example 34

The reaction was conducted according to the same manner as that of Example 30, except that 18.8 mg of 4,4'-bis(1,1-dimethylethyl)-2,2'-bipyridine was used in place of 12.9 mg of 5,5'-dimethyl-2,2'-bipyridine and 13.4 mg of 4,4'-difluoro-2,2'-bipyridine was used in place of 19.1 mg of 4,4'-bis(methoxycarbonyl9-2,2'-bipyridine, a reaction mixture containing a conjugated aromatic compound consisting of a repeating unit represented by the above-mentioned formula (ii) was obtained. Mw of the conjugated aromatic compound was 33,000, and Mn thereof was 13,000.

Example 35

The reaction was conducted according to the same manner as that of Example 30, except that 18.8 mg of 4,4'-bis(1,1-dimethylethyl)-2,2'-bipyridine was used in place of 12.9 mg of 5,5'-dimethyl-2,2'-bipyridine and 20.4 mg of 4,4-bis(trifluoromethyl)-2,2-bipyridine was used in place of 19.1 mg of 4,4'-bis(methoxycarbonyl)-2,2'-bipyridine, a reaction mixture containing a conjugated aromatic compound consisting of a repeating unit represented by the above-mentioned formula (ii) was obtained. Mw of the conjugated aromatic compound was 115,000, and Mn thereof was 36,000.

Comparative Example 36

The reaction was conducted according to the same manner as that of Example 30, except that 25.8 mg of 5,5'-dimethyl-2,2'-bipyridine was used in place of 12.9 mg of 5,5'-dimethyl-2,2'-bipyridine and 19.1 mg of 4,4'-bis(methoxycarbonyl)-2,2'-bipyridine, a reaction mixture containing a conjugated aromatic compound consisting of a repeating unit represented by the above-mentioned formula (ii) was obtained. Mw of the conjugated aromatic compound was 11,000, and Mn thereof was 8,000.

Comparative Example 37

The reaction was conducted according to the same manner as that of Example 30, except that 25.8 mg of 4,4'-dimethyl-2,2'-bipyridine was used in place of 12.9 mg of 5,5'-dimethyl-2,2'-bipyridine and 19.1 mg of 4,4'-bis(methoxycarbonyl)-2,2'-bipyridine, a reaction mixture containing a conjugated aromatic compound consisting of a repeating unit represented by the above-mentioned formula (ii) was obtained. Mw of the conjugated aromatic compound was 8,000, and Mn thereof was 6,000.

Comparative Example 38

The reaction was conducted according to the same manner as that of Example 30, except that 30.3 mg of 4,4'-dimethoxy-2,2'-bipyridine was used in place of 12.9 mg of 5,5'-dimethyl-2,2'-bipyridine and 19.1 mg of 4,4'-bis(methoxycarbonyl)-2,2'-bipyridine, a reaction mixture containing a conjugated aromatic compound consisting of a repeating unit represented by the above-mentioned formula (ii) was obtained. Mw of the conjugated aromatic compound was 5,000, and Mn thereof was 4,000.

Comparative Example 39

The reaction was conducted according to the same manner as that of Example 30, except that 37.6 mg of 4,4'-bis(1,1-dimethylethyl)-2,2'-bipyridine was used in place of 12.9 mg of 5,5'-dimethyl-2,2'-bipyridine and 19.1 mg of 4,4'-bis(methoxycarbonyl)-2,2'-bipyridine, a reaction mixture containing a conjugated aromatic compound consisting of a repeating unit represented by the above-mentioned formula (ii) was obtained. Mw of the conjugated aromatic compound was 21,000, and Mn thereof was 12,000.

Comparative Example 40

The reaction was conducted according to the same manner as that of Example 30, except that 38.1 mg of 4,4'-bis(methoxycarbonyl)-2,2'-bipyridine was used in place of 12.9 mg of 5,5'-dimethyl-2,2'-bipyridine and 19.1 mg of 4,4'-bis(methoxycarbonyl)-2,2'-bipyridine, a reaction mixture containing a conjugated aromatic compound consisting of a repeating unit represented by the above-mentioned formula (ii) was obtained. Mw of the conjugated aromatic compound was 29,000, and Mn thereof was 10,000.

Comparative Example 41

The reaction was conducted according to the same manner as that of Example 30, except that 26.9 mg of 4,4'-difluoro-2,2'-bipyridine was used in place of 12.9 mg of 5,5-dimethyl-2,2-bipyridine and 19.1 mg of 4,4'-bis(methoxycarbonyl)-2,2'-bipyridine, a reaction mixture containing a conjugated aromatic compound consisting of a repeating unit represented by the above-mentioned formula (ii) was obtained. Mw of the conjugated aromatic compound was 10,000, and Mn thereof was 8,000.

Example 36

To a reaction container made of glass and equipped with a cooling apparatus, 30.6 mg of nickel bromide, 18.8 mg of 4,4'-bis(1,1-dimethylethyl)-2,2'-bipyridine, 19.1 mg of 4,4'-bis(methoxycarbonyl)-2,2'-bipyridine, 109.9 mg of zinc powder, 2 mL of N,N-dimethylacetamide and a solution obtained by dissolving 287 mg of 1,7-heptanediol bis(m-chlorobenzoate) in 3 mL of N,N-dimethylacetamide were added in an atmosphere of nitrogen at room temperature. The reaction was conducted by stirring the mixture obtained at 70° C. for 4 hours to obtain a reaction mixture containing a conjugated aromatic compound consisting of the repeating unit represented by the following formula (iii). Mw of the conjugated aromatic compound was 36,000, and Mn thereof was 16,000.

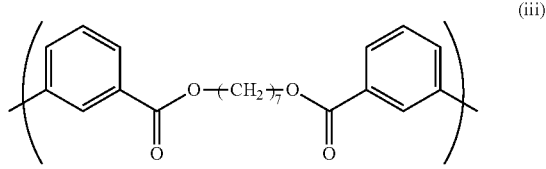

(iii)

Example 37

The reaction was conducted according to the same manner as that of Example 36, except that 13.4 mg of 4,4'-difluoro-2,2'-bipyridine was used in place of 19.1 mg of 4,4'-bis(methoxycarbonyl)-2,2'-bipyridine, a reaction mixture containing a conjugated aromatic compound consisting of a repeating unit represented by the above-mentioned formula (iii) was obtained. Mw of the conjugated aromatic compound was 22,000, and Mn thereof was 8,000.

Example 38

The reaction was conducted according to the same manner as that of Example 36, except that 20.4 mg of 4,4'-ditrifluoromethyl-2,2'-bipyridine was used in place of 19.1 mg of 4,4'-bis(methoxycarbonyl)-2,2'-bipyridine, a reaction mixture containing a conjugated aromatic compound consisting of a repeating unit represented by the above-mentioned formula (iii) was obtained. Mw of the conjugated aromatic compound was 19,000, and Mn thereof was 8,000.

Example 39

The reaction was conducted according to the same manner as that of Example 36, except that 19.1 mg of 5,5'-bis(methoxycarbonyl)-2,2'-bipyridine was used in place of 19.1 mg of 4,4'-bis(methoxycarbonyl)-2,2'-bipyridine, a reaction mixture containing a conjugated aromatic compound consisting of a repeating unit represented by the above-mentioned formula (iii) was obtained. Mw of the conjugated aromatic compound was 35,000, and Mn thereof was 16,000.

Comparative Example 42

The reaction was conducted according to the same manner as that of Example 36, except that 38.1 mg of 4,4'-bis(methoxycarbonyl)-2,2'-bipyridine was used in place of 18.8 mg of 4,4'-bis(1,1-dimethylethyl)-2,2-bipyridine and 19.1 mg of 4,4'-bis(methoxycarbonyl)-2,2'-bipyridine, a reaction mixture containing a conjugated aromatic compound consisting of a repeating unit represented by the above-mentioned formula (iii) was obtained. Mw of the conjugated aromatic compound was 2,000, and Mn thereof was 2,000.

Comparative Example 43

The reaction was conducted according to the same manner as that of Example 36, except that 38.1 mg of 5,5'-bis(methoxycarbonyl)-2,2'-bipyridine was used in place of 18.8 mg of 4,4'-bis(1,1-dimethylethyl)-2,2'-bipyridine and 19.1 mg of 4,4'-bis(methoxycarbonyl)-2,2'-bipyridine, a reaction mixture containing a conjugated aromatic compound consisting of a repeating unit represented by the above-mentioned formula (iii) was obtained. Mw of the conjugated aromatic compound was 2,000, and Mn thereof was 2,000.

Comparative Example 44

The reaction was conducted according to the same manner as that of Example 36, except that 26.9 mg of 4,4'-difluoro-2,2'-bipyridine was used in place of 18.8 mg of 4,4'-bis(1,1-dimethylethyl)-2,2'-bipyridine and 19.1 mg of 4,4'-bis(methoxycarbonyl)-2,2'-bipyridine, a reaction mixture containing a conjugated aromatic compound consisting of a repeating unit represented by the above-mentioned formula (iii) was obtained. Mw of the conjugated aromatic compound was 16,000, and Mn thereof was 7,000.

Comparative Example 45

The reaction was conducted according to the same manner as that of Example 36, except that 40.9 mg of 4,4'-bis(trifluoromethyl)-2,2'-bipyridine was used in place of 18.8 mg of 4,4'-bis(1,1-dimethylethyl)-2,2'-bipyridine and 19.1 mg of 4,4'-bis(methoxycarbonyl)-2,2'-bipyridine, a reaction mixture containing a conjugated aromatic compound consisting of a repeating unit represented by the above-mentioned formula (iii) was obtained. Mw of the conjugated aromatic compound was 3,000, and Mn thereof was 2,000.

Comparative Example 46

The reaction was conducted according to the same manner as that of Example 36, except that 37.6 mg of 4,4'-bis(1,1-dimethylethyl)-2,2'-bipyridine was used in place of 18.8 mg of 4,4'-bis(1,1-dimethylethyl)-2,2'-bipyridine and 19.1 mg of 4,4'-bis(methoxycarbonyl)-2,2'-bipyridine, a reaction mixture containing a conjugated aromatic compound consisting of a repeating unit represented by the above-mentioned formula (iii) was obtained. Mw of the conjugated aromatic compound was 20,000, and Mn thereof was 8,000.

Example 40

To a reaction container made of glass and equipped with a cooling apparatus, 30.6 mg of nickel bromide, 15.1 mg of 4,4'-dimethoxy-2,2'-bipyridine, 19.1 mg of 4,4'-bis(methoxycarbonyl)-2,2'-bipyridine, 109.9 mg of zinc powder, 2 mL of N,N-dimethylacetamide and a solution obtained by dissolving 167 mg of 1,4-dichloro-2-phenoxybenzene in 3 mL of N,N-dimethylacetamide were added in an atmosphere of nitrogen at room temperature. The reaction was conducted by stirring the mixture obtained at 70° C. for 4 hours to obtain a reaction mixture containing a conjugated aromatic compound consisting of the repeating unit represented by the following formula (iv). Mw of the conjugated aromatic compound was 9,000, and Mn thereof was 5,000.

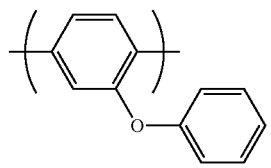

Comparative Example 47

The reaction was conducted according to the same manner as that of Example 40, except that 30.3 mg of 4,4'-dimethoxy-2,2'-bipyridine was used in place of 15.1 mg of 4,4'-dimethoxy-2,2'-bipyridine and 19.1 mg of 4,4'-bis(methoxycarbonyl)-2,2'-bipyridine, a reaction mixture containing a conjugated aromatic compound consisting of a repeating unit represented by the above-mentioned formula (iv) was obtained. Mw of the conjugated aromatic compound was 2,000, and Mn thereof was 2,000.

Comparative Example 48

The reaction was conducted according to the same manner as that of Example 40, except that 38.1 mg of 4,4'-bis(methoxycarbonyl)-2,2-bipyridine was used in place of 15.1 mg of 4,4'-dimethoxy-2,2'-bipyridine and 19.1 mg of 4,4'-bis(methoxycarbonyl)-2,2'-bipyridine, a reaction mixture containing a conjugated aromatic compound consisting of a repeating unit represented by the above-mentioned formula (iv) was obtained. Mw of the conjugated aromatic compound was 2,000, and Mn thereof was 2,000.

Example 41

To a reaction container made of glass and equipped with a cooling apparatus, 30.6 mg of nickel bromide, 11.4 mg of 4,4'-bis(1,1-dimethylethyl)-2,2'-bipyridine, 26.3 mg of 4,4'-bis(methoxycarbonyl)-2,2'-bipyridine, 109.9 mg of zinc powder, 2 mL of N,N-dimethylacetamide and a solution obtained by dissolving 175 mg of 3,5-dibromotoluene in 3 mL of N,N-dimethylacetamide were added in an atmosphere of nitrogen at room temperature. The reaction was conducted by stirring the mixture obtained at 70° C. for 4 hours to obtain a reaction mixture containing a conjugated aromatic compound consisting of the repeating unit represented by the following formula (v). Mw of the conjugated aromatic compound was 10,000, and Mn thereof was 6,000.

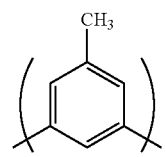

Comparative Example 49

The reaction was conducted according to the same manner as that of Example 41, except that 37.6 mg of 4,4'-bis(1,1-dimethylethyl)-2,2'-bipyridine was used in place of 11.4 mg of 4,4'-bis(1,1-dimethylethyl)-2,2'-bipyridine and 26.3 mg of 4,4'-bis(methoxycarbonyl)-2,2'-bipyridine, a reaction mixture containing a conjugated aromatic compound consisting of a repeating unit represented by the above-mentioned formula (v) was obtained. Mw of the conjugated aromatic compound was 2,000, and Mn thereof was 2,000.

Comparative Example 50

The reaction was conducted according to the same manner as that of Example 41, except that 38.1 mg of 4,4'-bis(methoxycarbonyl)-2,2'-bipyridine was used in place of 11.4 mg of 4,4'-bis(1,1-dimethylethyl)-2,2'-bipyridine and 26.3 mg of 4,4'-bis(methoxycarbonyl)-2,2'-bipyridine, a reaction mixture containing a conjugated aromatic compound consisting of a repeating unit represented by the above-mentioned formula (v) was obtained. Mw of the conjugated aromatic compound was 9,000, and Mn thereof was 4,000.

Example 42

To a reaction container made of glass and equipped with a cooling apparatus, 30.6 mg of nickel bromide, 11.4 mg of 4,4'-bis(1,1-dimethylethyl)-2,2'-bipyridine, 26.3 mg of 4,4'-bis(methoxycarbonyl)-2,2'-bipyridine, 109.9 mg of zinc powder, 2 mL of N,N-dimethylacetamide and a solution obtained by dissolving 177 mg of 3,5-dichloroanisole in 3 mL of N,N-dimethylacetamide were added in an atmosphere of nitrogen at room temperature. The reaction was conducted by stirring the mixture obtained at 70° C. for 4 hours to obtain a reaction mixture containing a conjugated aromatic compound consisting of the repeating unit represented by the following formula (vi). Mw of the conjugated aromatic compound was 18,000, and Mn thereof was 10,000.

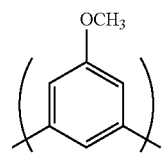

(vi)

Comparative Example 51

The reaction was conducted according to the same manner as that of Example 41, except that 37.6 mg of 4,4'-bis(1,1-dimethylethyl)-2,2'-bipyridine was used in place of 11.4 mg of 4,4'-bis(1,1-dimethylethyl)-2,2'-bipyridine and 26.3 mg of 4,4'-bis(methoxycarbonyl)-2,2'-bipyridine, a reaction mixture containing a conjugated aromatic compound consisting of a repeating unit represented by the above-mentioned formula (vi) was obtained. Mw of the conjugated aromatic compound was 14,000, and Mn thereof was 6,000.

Comparative Example 52

The reaction was conducted according to the same manner as that of Example 41, except that 38.1 mg of 4,4'-bis(methoxycarbonyl)-2,2'-bipyridine was used in place of 11.4 mg of 4,4'-bis(1,1-dimethylethyl)-2,2'-bipyridine and 26.3 mg of 4,4'-bis(methoxycarbonyl)-2,2'-bipyridine, a reaction mixture containing a conjugated aromatic compound consisting of a repeating unit represented by the above-mentioned formula (vi) was obtained. Mw of the conjugated aromatic compound was 2,000, and Mn thereof was 2,000.

Example 43

To a reaction container made of glass and equipped with a cooling apparatus, 7.6 mg of nickel bromide, 4.7 mg of 4,4'-bis(1,1-dimethylethyl)-2,2'-bipyridine, 4.8 mg of 4,4'-bis(methoxycarbonyl)-2,2'-bipyridine, 96 mg of zinc powder, a solution obtained by dissolving 366 mg of di(2,2-dimethylpropyl) 4,4'-dichlorobiphenyl-2,2'-sulfonate in 3 mL of N,N-dimethylacetamide and a solution obtained by dissolving 100 mg of SUMIKA EXCEL PES 3100P represented by the following formula (vii):

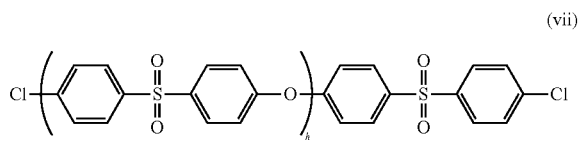

which have been manufactured by Sumitomo Chemical Company, Limited; Mw 36,000 and Mn 18,000 which had been measured by the above analytical condition, in 2 mL of N,N-dimethylacetamide were added in an atmosphere of nitrogen at room temperature. The reaction was conducted by stirring the mixture obtained at 70° C. for 4 hours to obtain a reaction mixture containing a conjugated aromatic compound consisting of the repeating unit represented by the above-mentioned formula (I) and a segment represented by the following formula:

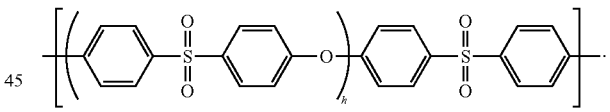

Mw of the conjugated aromatic compound was 268,000, and Mn thereof was 84,000.

Example 44

The reaction was conducted according to the same manner as that of Example 43, except that 100 mg of an aromatic compound represented by the following formula (viii)

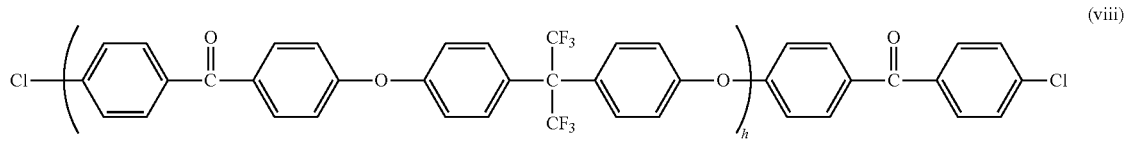

of which Mw was 6,500 and Mn was 4,700 which had been measured by the above analytical condition, in place of 100 mg of SUMIKA EXCEL PES 3100P, a reaction mixture containing a conjugated aromatic compound consisting of a repeating unit represented by the above-mentioned formula (i) and a segment represented by the following formula:

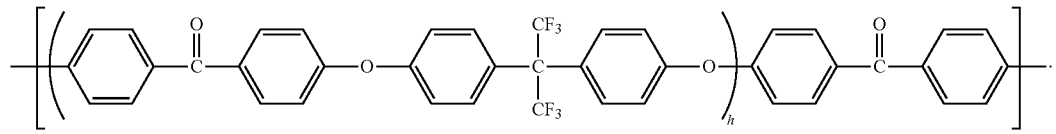

Mw of the conjugated aromatic compound was 353,000, and Mn thereof was 106,000.

Example 45

The reaction was conducted according to the same manner as that of Example 43, except that 100 mg of polyphenylsulfone represented by the following formula (ix)

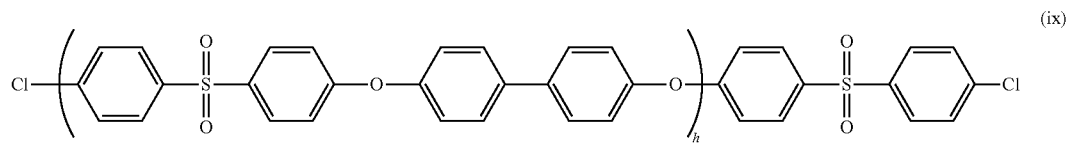

(ix)

which had been manufactured by Aldrich, and of which Mw was 49,000 and Mn was 18,000 which had been measured by the above analytical condition, in place of 100 mg of SUMIKA EXCEL PES 3100P, a reaction mixture containing a conjugated aromatic compound consisting of a repeating unit represented by the above-mentioned formula (i) and a segment represented by the following formula:

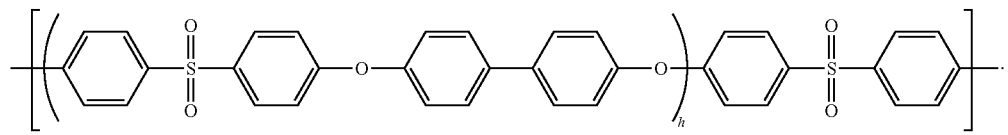

Mw of the conjugated aromatic compound was 246,000, and Mn thereof was 71,000.

Example 46

The reaction was conducted according to the same manner as that of Example 43, except that 100 mg of polysulfone represented by the following formula (x)

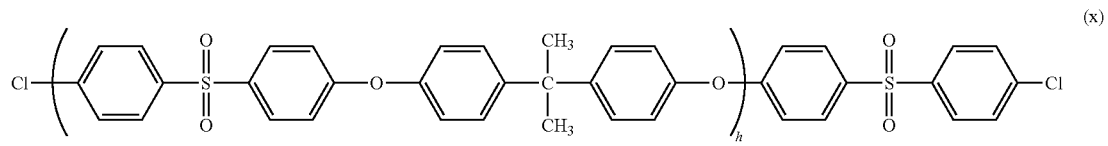

(x)

which had been manufactured by Aldrich, and of which Mw was 63,000 and Mn was 31,000 which had been measured by the above analytical condition, in place of 100 mg of SUMIKA EXCEL PES 3100P, a reaction mixture containing a conjugated aromatic compound consisting of a repeating unit represented by the above-mentioned formula (i) and a segment represented by the following formula:

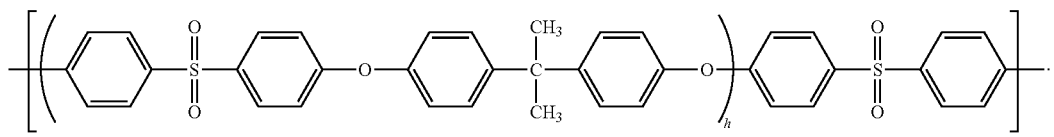

Mw of the conjugated aromatic compound was 236,000, and Mn thereof was 75,000.

Example 47

The reaction was conducted according to the same manner as that of Example 14, except that 4.1 mg of 3,4,7,8-tetramethyl-1,10-phenanthroline was used in place of 4.7 mg of 4,4'-bis(1,1-dimethylethyl)-2,2'-bipyridine, a reaction mixture containing a conjugated aromatic compound consisting of a repeating unit represented by the above-mentioned formula (i) was obtained. Mw of the conjugated aromatic compound was 515,000, and Mn thereof was 116,000.

Comparative Example 53

The reaction was conducted according to the same manner as that of Example 14, except that 8.3 mg of 3,4,7,8-tetramethyl-1,10-phenanthroline was used in place of 4.7 mg of 4,4'-bis(1,1-dimethylethyl)-2,2'-bipyridine and 4.7 mg of 4,4'-bis(methoxycarbonyl)-2,2'-bipyridine, a reaction mixture containing a conjugated aromatic compound consisting of a repeating unit represented by the above-mentioned formula (i) was obtained. Mw of the conjugated aromatic compound was 2,000, and Mn thereof was 2,000.

INDUSTRIAL APPLICABILITY

According to the present invention, a conjugated aromatic compound can be produced more advantageously.

The invention claimed is:

1. A method for manufacturing a conjugated aromatic compound comprising reacting a first aromatic compound comprising an aromatic ring with a second aromatic compound comprising an aromatic ring in the presence of (i) a nickel compound, (ii) a metal reducing agent, (iii) at least one ligand (L1) selected from the group consisting of a 2,2'-bipyridine compound having at least one electron-withdrawing group and having no substituent at 3-, 6-, 3'- and 6'-positions, and a 1,10-phenanthroline compound having at least one electron-withdrawing group and having no substituent at 2- and 9-positions, and (iv) at least one ligand (L2) selected from the group consisting of a 2,2'-bipyridine compound having at least one electron-releasing group and having no substituent at 3-, 6-, 3'- and 6'-positions, and a 1,10-phenanthroline compound having at least one electron-releasing group and having no substituent at 2- and 9-positions, wherein the first aromatic ring comprises one or two leaving groups selected from the group consisting of an iodine atom, a bromine atom and a chlorine atom bonded thereto;

wherein the first aromatic ring does not comprise a group (c1), (g1) or (h1) at the neighboring carbon atom to the carbon atom to which the leaving group is bonded;

wherein (c1) is represented by the following formula (10):

(10)

wherein $A^1$ represents an amino group substituted with one or two C1-C20 hydrocarbon groups or a C1-C20 alkoxy group, wherein the hydrocarbon group and the alkoxy group may be substituted with at least one group selected from the group consisting of a fluorine atom, a C1-C20 alkoxy group, a C6-C20 aryl group, a C6-C20 aryloxy group, a C2-C20 acyl group and a C6-C20 arylsulfonyl group;

wherein (g1) consists of a C1-C20 alkyl group which may be substituted with at least one substituent selected from the group consisting of a fluorine atom, a cyano group, a C1-C20 alkoxy group, a C6-C20 aryl group and a C6-C20 aryloxy group; and wherein (h1) consists of a C2-C20 acyl group which may be substituted with at least one substituent selected from the group consisting of a fluorine atom, a cyano group, a C1-C20 alkoxy group, a C6-C20 aryl group and a C6-C20 aryloxy group;

wherein the second aromatic ring has the same structure as the first aromatic ring or a different structure from the first aromatic ring;

wherein the second aromatic ring comprises one or two leaving groups selected from the group consisting of an iodine atom, a bromine atom and a chlorine atom bonded thereto, wherein the second aromatic ring does not comprise the (c1), (g1) and (h1) at the neighboring carbon atom to the carbon atom to which the leaving group is bonded; and wherein the first aromatic ring and the second aromatic ring are independently selected from the group consisting of a benzene ring, a biphenyl ring, a naphthalene ring, a fluorene ring, an anthracene ring, a phenanthrene ring, a thiophene ring, a pyrrole ring and a pyridine ring.

2. The method according to claim 1, wherein the ligand (L1) is at least one ligand selected from the group consisting of a 2,2'-bipyridine compound having at least two electron-withdrawing groups and having no substituent at 3-, 6-, 3'- and 6'-positions, and a 1,10-phenanthroline compound having at least two electron-withdrawing groups and having no substituent at 2- and 9-positions.

3. The method according to claim 1, wherein the ligand (L1) is a 2,2'-bipyridine compound having at least two electron-withdrawing groups and having no substituent at 3-, 6-, 3'- and 6'-positions.

4. The method according to claim 1, wherein the ligand (L2) is at least one ligand selected from the group consisting of a 2,2'-bipyridine compound having at least two electron-releasing groups and having no substituent at 3-, 6-, 3'- and 6'-positions, and a 1,10-phenanthroline compound having at least two electron-releasing groups and having no substituent at 2- and 9-positions.

5. The method according to claim 1, wherein the ligand (L2) is a 2,2'-bipyridine compound having at least two electron-releasing groups and having no substituent at 3-, 6-, 3'- and 6'-positions.

6. The method according to claim 2, wherein the 2,2'-bipyridine compound having at least two electron-withdrawing groups and having no substituent at 3-, 6-, 3'- and 6'-positions is a bipyridine compound represented by the formula (1)

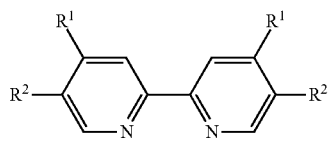

wherein $R^1$ and $R^2$ independently each represent a hydrogen atom or an electron-withdrawing group, with the proviso that $R^1$ and $R^2$ are not hydrogen atoms simultaneously.

7. The method according to claim 2, wherein the 1,10-phenanthroline compound having at least two electron-withdrawing groups and having no substituent at 2- and 9-positions is a phenanthroline compound represented by the formula (2)

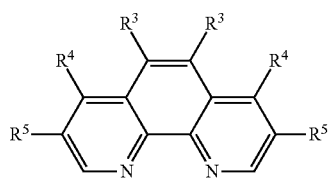

wherein $R^3$, $R^4$ and $R^5$ independently each represent a hydrogen atom or an electron-withdrawing group, with the proviso that $R^3$, $R^4$ and $R^5$ are not hydrogen atoms simultaneously.

8. The method according to claim 4, wherein the 2,2'-bipyridine compound having at least two electron-releasing groups and having no substituent at 3-, 6-, 3'- and 6'-positions is a bipyridine compound represented by the formula (3)

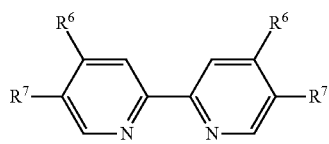

wherein $R^6$ and $R^7$ independently each represent a hydrogen atom or an electron-releasing group, with the proviso that $R^6$ and $R^7$ are not hydrogen atoms simultaneously.

9. The method according to claim 4, wherein the 1,10-phenanthroline compound having at least two electron-releasing groups and having no substituent at 2- and 9-positions is a phenanthroline compound represented by the formula (4)

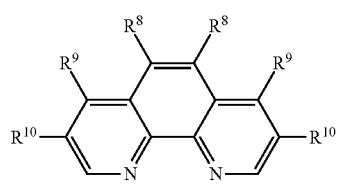

wherein $R^8$, $R^9$ and $R^{10}$ independently each represent a hydrogen atom or an electron-releasing group, with the proviso that $R^8$, $R^9$ and $R^{10}$ are not hydrogen atoms simultaneously.

10. The method according to claim 1, wherein the electron-withdrawing group is a fluorine atom, a C1-C20 fluorinated alkyl group, a C2-C20 alkoxycarbonyl group, a C2-C20 acyl group, a cyano group or a nitro group.

11. The method according to claim 1, wherein the electron-releasing group is a C1-C20 alkyl group, a C1-C20 alkoxy group, a C6-C20 aryl group or a C1-C20 dialkylamino group.

12. The method according to claim 1, wherein the second aromatic ring has the same structure as the first aromatic ring.

13. The method according to claim 1, wherein the second aromatic ring has a different structure from the first aromatic ring.

14. The method according to claim 12, wherein the first aromatic compound is an aromatic compound represented by the formula (5)

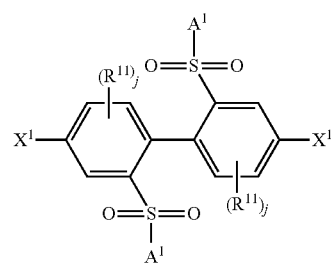

wherein $A^1$ represents an amino group substituted with one or two C1-C20 hydrocarbon groups, or a C1-C20 alkoxy group, and the above-mentioned hydrocarbon group and the above-mentioned alkoxy group may be substituted with at least one group selected from the group consisting of a fluorine atom, a C1-C20 alkoxy group, a C6-C20 aryl group, a C6-C20 aryloxy group, a C2-C20 acyl group and a C6-C20 arylsulfonyl group, $R^{11}$ is independently in each occurrence a fluorine atom, a C1-C20 alkyl group, a C1-C20 alkoxy group, a C6-C20 aryl group, a C6-C20 aryloxy group, a C2-C20 acyl group or a cyano group, and the above-mentioned C1-C20 alkyl group, the above-mentioned C1-C20 alkoxy group, the above-mentioned C6-C20 aryl group, the above-mentioned C6-C20 aryloxy group and the above-mentioned C2-C20 acyl group may be substituted with at least one substituent selected from the group consisting of a fluorine atom, a cyano group, a C1-C20 alkoxy group, a C6-C20 aryl group and a C6-C20 aryloxy group, and $R^{11}$s being bonded to the neighboring two carbon atoms may be bonded to form a ring, with the proviso that when $R^{11}$ is a C1-C20 alkyl group or a C2-C20 acyl group, $R^{11}$ is bonded to a carbon atom other than the neighboring carbon atoms to the carbon atom to which $X^1$ is bonded, $X^1$ represents a chlorine atom, a bromine atom or an iodine atom, and j represents an integer of 0 to 3.

15. The method according to claim 13, wherein as the aromatic compound, an aromatic compound represented by the formula (6)

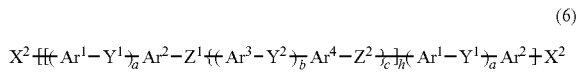

(6)

wherein a, b and c are the same or different and represent 0 or 1, and h represents an integer of 5 or more, $Ar^1$, $Ar^2$, $Ar^3$ and $Ar^4$ independently each represent a divalent aromatic group, and the divalent aromatic group may be substituted with at least one substituent selected from the group consisting of the following (a2) to (e2):

(a2) a C1-C20 alkyl group which may be substituted with at least one substituent selected from the group consisting of a fluorine atom, a cyano group, a C1-C20 alkoxy group, a C6-C20 aryl group and a C6-C20 aryloxy group;

(b2) a C1-C20 alkoxy group which may be substituted with at least one substituent selected from the group consisting of a fluorine atom, a cyano group, a C1-C20 alkoxy group, a C6-C20 aryl group and a C6-C20 aryloxy group;

(c2) a C6-C20 aryl group which may be substituted with at least one substituent selected from the group consisting of a fluorine atom, a cyano group, a C1-C20 alkoxy group and a C6-C10 aryloxy group;

(d2) a C6-C20 aryloxy group which may be substituted with at least one substituent selected from the group consisting of a fluorine atom, a cyano group, a C1-C20 alkoxy group and a C6-C20 aryloxy group; and (e2) a C2-C20 acyl group which may be substituted with at least one substituent selected from the group consisting of a fluorine atom, a cyano group, a C1-C20 alkoxy group, a C6-C20 aryl group and a C6-C20 aryloxy group, with the proviso that (a2) and (e2) are not bonded to the neighboring carbon atoms to the carbon atoms of $Ar^1$ and $Ar^2$ to which $X^2$ is bonded, $Y^1$ and $Y^2$ independently each represent a single bond, —CO—, —SO$_2$—, —C(CH$_3$)$_2$—, —C(CF$_3$)$_2$— or a fluorene-9,9-diyl group, $Z^1$ and $Z^2$ independently each represent —O— or —S—, and $X^2$ represents a chlorine atom, a bromine atom or an iodine atom, is used.

16. The method according to claim 1, wherein the nickel compound is a nickel halide.

17. The method according to claim 1, wherein the nickel compound is bis(cyclooctadiene)nickel(0).

18. The method according to claim 1, wherein the metal reducing agent is zinc.

* * * * *